(12) United States Patent
Dilger et al.

(10) Patent No.: US 6,345,234 B1
(45) Date of Patent: Feb. 5, 2002

(54) FUGITIVE EMISSION SENSING SYSTEM

(75) Inventors: John Patrick Dilger; Ted D. Grabau, both of Marshalltown; Nile K. Dielschneider, Conrad; Meredith D. Miller, Marshalltown, all of IA (US)

(73) Assignee: Fisher Controls International, Inc., Marshalltown, IA (US)

( * ) Notice: Subject to any disclaimer, the term of this patent is extended or adjusted under 35 U.S.C. 154(b) by 0 days.

(21) Appl. No.: 09/189,671

(22) Filed: Nov. 11, 1998

Related U.S. Application Data

(60) Provisional application No. 60/065,349, filed on Nov. 12, 1997.

(51) Int. Cl.⁷ .................. G01N 31/00; G06F 19/00
(52) U.S. Cl. ................... 702/24; 702/30; 73/23.31
(58) Field of Search .................. 702/22–27, 30–32, 702/50, 51, 85, 90, 91, 104, 127–129, 185; 73/23.31; 340/632, 634, 605

(56) References Cited

U.S. PATENT DOCUMENTS

| | | | | |
|---|---|---|---|---|
| 3,630,072 A | * | 12/1971 | Traver | 73/23.21 |
| 3,694,107 A | * | 9/1972 | Stein | 417/167 |
| 4,138,891 A | * | 2/1979 | Graves et al. | 73/864.73 |
| 4,204,121 A | * | 5/1980 | Milly | 250/343 |
| 4,441,356 A | | 4/1984 | Bohl | 73/23 |
| 4,449,506 A | * | 5/1984 | Drutchas | 123/458 |
| 4,534,662 A | * | 8/1985 | Barlian | 374/4 |
| 4,901,751 A | | 2/1990 | Story et al. | 137/312 |
| 4,972,867 A | | 11/1990 | Ruesch | 137/15 |
| 5,056,355 A | * | 10/1991 | Hepher et al. | 73/24.03 |
| 5,249,954 A | * | 10/1993 | Allen et al. | 431/14 |
| 5,417,105 A | | 5/1995 | Martinez et al. | 73/40.7 |
| 5,469,731 A | * | 11/1995 | Decker et al. | 73/23.31 |
| 5,533,890 A | * | 7/1996 | Holst et al. | 431/5 |
| 5,610,324 A | * | 3/1997 | Lawson | 73/46 |
| 5,610,835 A | * | 3/1997 | Dominguez et al. | 702/24 |
| 5,734,098 A | * | 3/1998 | Kraus et al. | 73/61.62 |
| 5,739,413 A | * | 4/1998 | Kohn et al. | 73/23.21 |
| 6,029,506 A | * | 2/2000 | Dilger | 73/46 |

FOREIGN PATENT DOCUMENTS

| | | | |
|---|---|---|---|
| EP | 0-503-841 A2 | 9/1992 | G01N/1/26 |
| EP | 0-710-829 A1 | 11/1994 | G01N/1/24 |
| GB | 0503841 A2 * | 9/1992 | |

* cited by examiner

Primary Examiner—Marc S. Hoff
Assistant Examiner—Manuel L. Barbee
(74) Attorney, Agent, or Firm—Howrey Simon Arnold & White LLP

(57) ABSTRACT

A system and method for collecting data relating to emissions from an emissions source is disclosed. The system comprises an accumulator adapted to receive emissions from the emissions source, a sensor in flow communication with an outlet of the accumulator for generating a signal indicative of a physical property of the emissions, and a sensor interface circuit receiving the signal and generating data relating to the emissions from the emissions source.

A system and method for reducing emissions from an emissions source is also disclosed, including a microcontroller receiving data relating to the emissions from the emissions source and generating control signals for reducing the emissions.

47 Claims, 17 Drawing Sheets

FUGITIVE EMISSION SENSING SYSTEM

CROSS-REFERENCE TO RELATED APPLICATIONS

This application claims the benefit of the filing date of provisional application Ser. No. 60/065,349, filed Nov. 12, 1997, entitled "Fugitive Emission Sensing System," for all subject matter disclosed in the provisional application.

This application is related to copending application Ser. No. 08/968,081, filed Nov. 12, 1997, entitled "High Frequency Measuring Circuit," copending application Ser. No. 08/968,545, filed Nov. 12, 1997, entitled "Sample Retrieval System," and copending application Ser. No. 08/967,870, filed Nov. 12, 1997, entitled "Thermally Activated Calibration System for Chemical Sensors," all commonly assigned with the present invention.

BACKGROUND OF THE INVENTION

A. Field of the Invention

The present invention relates generally to systems for monitoring environmental contaminants and, more particularly, to systems for measuring fugitive emissions from process equipment.

B. Description of the Related Art

Industrial plants that handle volatile organic compounds (VOCs) typically experience unwanted emissions of those compounds into the atmosphere from point sources such as smokestacks and non-point sources such as valves, pumps, and fittings installed in pipes and vessels containing the VOCs. Emissions from non-point sources, referred to as "fugitive" emissions, typically occur due to leakage of the VOCs from joints and seals. Fugitive emissions from control valves may occur as leakage through the packing between the valve stem and body/bonnet of the valve. Valves employed in demanding service conditions involving frequent movement of the valve stem and large temperature fluctuations typically suffer accelerated deterioration of the valve stem packing, resulting in greater fugitive emissions than valves in less demanding service.

While improvements in valve stem packing materials and designs have reduced fugitive emissions and lengthened the life of valve packing, the monitoring of fugitive emissions has become important as a means to identify and reduce fugitive emissions and comply with new more stringent regulation of emissions. The Environmental Protection Agency (EPA) has promulgated regulations specifying the maximum permitted leakage of certain hazardous air pollutants from control valves, and requiring periodic surveys of emissions from control valves.

Current methods of monitoring fugitive emissions involve manual procedures using a portable organic vapor analyzer. This manual method is time consuming and expensive to perform, and can also yield inaccurate results due to ineffective collection of the fugitive emissions from the equipment being monitored. If measurements are made on a valve exposed to wind, emissions from the valve may be dissipated before the vapor analyzer can properly measure the concentration of the emissions. Also, if the analyzer is not carefully moved around the valve to capture all the emissions from the valve, an inaccurate measurement will result. Manual measurement methods also require plant personnel to dedicate a significant amount of time to making the measurements, distracting from their other duties.

Automated monitoring and detection of fugitive emissions can yield significant advantages over existing manual methods. The EPA regulations require surveys of fugitive emissions at periodic intervals. The length of the survey interval may be monthly, quarterly, semi-annual, or annual; the required surveys becoming less frequent if the facility operator can document fewer than a certain percentage of control valves with excessive leakage. Thus, achieving a low percentage of leaking valves reduces the number of surveys required per year. In a large industrial facility where the total number of survey points can range from 50,000 to 200,000 points, this can result in large cost savings. By installing automated fugitive emission sensing systems onto valves subject to the most demanding service conditions and thus most likely to develop leaks, compliance with the EPA regulations can be more readily achieved for the entire facility. This results in longer intervals between surveys for all of the valves, significantly reducing the time and expense of taking measurements manually from the valves without automated sensing systems.

Early detection of fugitive emissions from leaking valves also enables repairs to be made on a more timely basis, reducing the quantity of hazardous material emitted and reducing the cost of lost material. Accurate sensing of fugitive emissions provides an early warning system which can alert the facility operator to a potential valve seal failure and enable preventive measures to be taken before excessive leakage occurs.

However, employing an automated fugitive emission sensing system in an industrial environment requires designing a sample retrieval system which can efficiently collect fugitive emissions emanating from a piece of equipment and transport the emissions to gas sensors. The sample retrieval system must be capable of delivering a sample stream at a known flow rate in order to permit the gas sensors to make accurate and consistent measurements of the concentration of fugitive emissions.

Furthermnore, employing gas sensors in an industrial environment requires designing sensors that perform satisfactorily in the presence of high relative humidity (up to 85%) through a broad temperature range (from −40° C. to +85° C.). The sensors must be able to discriminate between the emissions of interest and other environmental contaminants, while retaining sufficient sensitivity to detect low concentrations of the fugitive emissions. Provision also must be made to enable periodic calibration of the gas sensors. The output signals from the fugitive emission sensing system must be suitable for input into plant monitoring and control systems typically found in process plants. This will permit simple and inexpensive integration of the sensing system into existing plant process control systems.

The fugitive emission sensing system must be inexpensive to manufacture, and use a power source that is readily available in a typical process plant, in order to keep installation costs to a minimum. The system must be suitable for use in hazardous areas subject to a risk of explosion, requiring electrical equipment to be of intrinsically safe or explosion-proof design. It also must be able to operate in harsh environments, including areas subject to spray washing, high humidity, high and low temperatures, and vibration. The system also must be simple and reliable, in order to keep maintenance costs to a minimum.

Accordingly, it is an object of the present invention to provide an apparatus and method that addresses the concerns set forth above.

SUMMARY OF THE INVENTION

According to one aspect of the present invention, a system for collecting data relating to emissions from an emissions source comprises an accumulator adapted to receive emissions from the emissions source, a sensor in flow communication with an outlet of the accumulator for generating a signal indicative of a physical property of the emissions, and a sensor interface circuit receiving the signal and generating data relating to the emissions from the emissions source. In a particular embodiment, the accumulator comprises a collecting tube, and in another embodiment, the accumulator comprises a bonnet capsule.

In accordance with another aspect of the invention, the system includes an ejector in flow communication with the outlet of the accumulator. The ejector draws the emissions from the accumulator to expose the sensor to the emissions. The ejector may be connected to a source of pressurized fluid so that the pressurized fluid flows through the ejector thereby creating a pressure drop to draw the emissions from the accumulator into the ejector.

In accordance with another aspect of the invention, the system includes a sensor calibrator in flow communication with the at least one sensor for storing a calibrant and exposing the at least one sensor to the calibrant.

In accordance with another aspect of the invention, the system provides that data generated by the sensor interface circuit is derived by measuring the frequency of said signal generated by the sensor.

In accordance with another aspect of the invention, the system includes a microcontroller adapted to receive the data from the sensor interface circuit, and a memory connected to the microcontroller for storing data from the sensor interface circuit where the data is derived from the at least one sensor's response to the calibrant.

In accordance with another aspect of the invention, a system for reducing emissions from an emissions source comprises an accumulator adapted to receive emissions from the emissions source, a sensor in flow communication with an outlet of the accumulator for generating a signal indicative of a physical property of the emissions, a sensor interface circuit receiving the signal for generating data relating to the emissions from the emissions source, and a microcontroller receiving the data for generating control signals for reducing emissions from the emissions source.

In accordance with another aspect of the invention, a method for collecting data relating to emissions from an emissions source comprises collecting at least a portion of the emissions, exposing at least one sensor to the emissions to generate a signal indicative of a physical property of the emissions, and processing the signal generated by the at least one sensor to generate data relating to the emissions from the emissions source.

In accordance with another aspect of the invention, a method for reducing emissions from an emissions source comprises situating an accumulator adjacent the emissions source to receive the emissions, providing at least one sensor in flow communication with the accumulator, exposing the at least one sensor to the emissions to generate a signal indicative of a physical property of the emissions, and processing the signal generated by the at least one sensor to generate control signals for controlling plant conditions to reduce the emissions from the emissions source.

BRIEF DESCRIPTION OF THE DRAWINGS

The features and advantages of the present invention will be best appreciated upon reference to the following detailed description and the accompanying drawings, in which.

Figure 1:
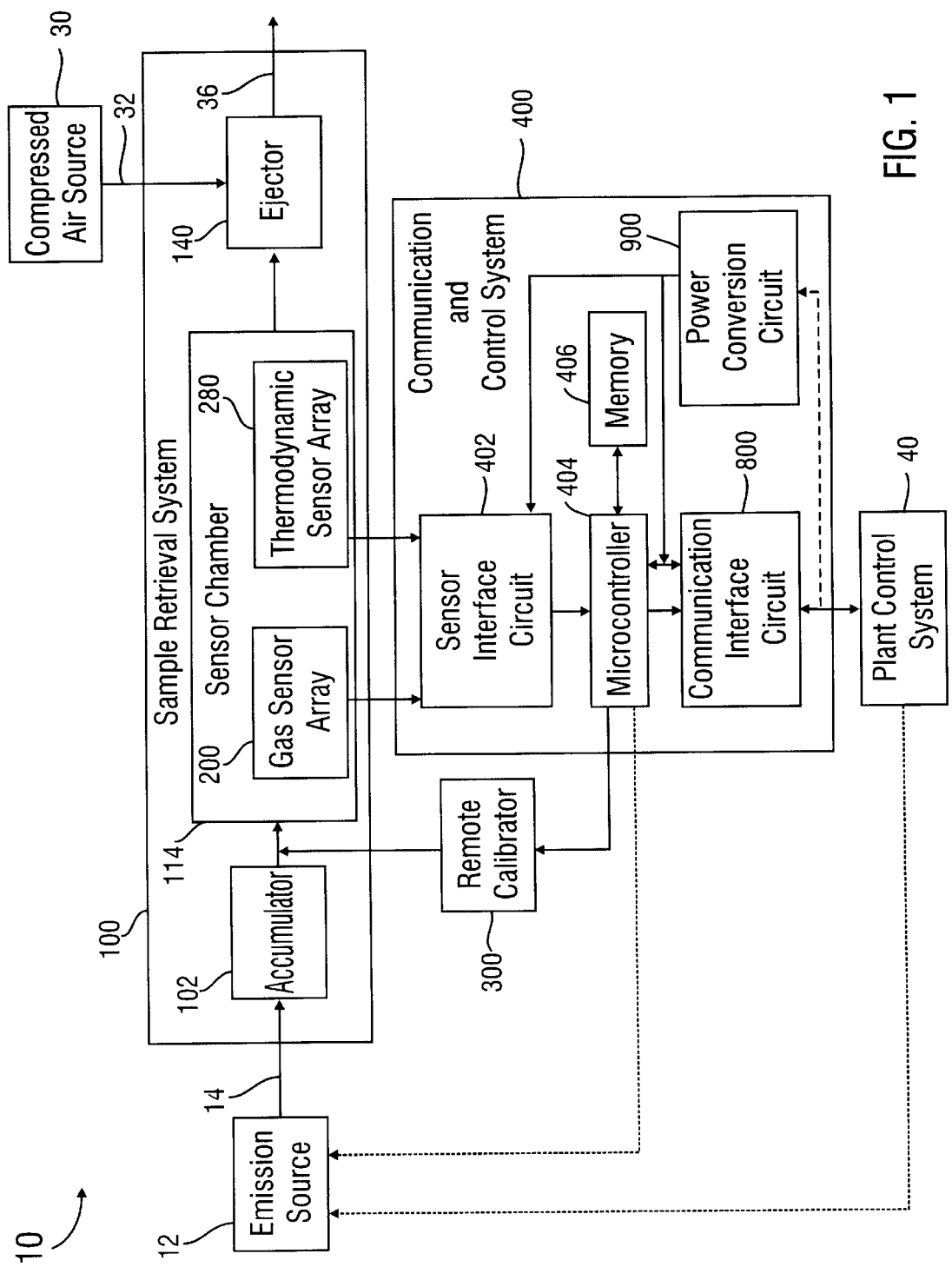
FIG. 1 is a block diagram of an illustrative embodiment of the invention showing the major components of a fugitive emission sensing system.

While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention as defined by the appended claims.

DETAILED DESCRIPTION OF THE INVENTION

A. FUGITIVE EMISSION SENSING SYSTEM

Turning now to the drawings and referring initially to FIG. 1, a block diagram of an illustrative embodiment of the invention is given showing the major components of a fugitive emission sensing system 10. An emission source 12 is shown, from which a sample stream 14 is drawn into sample retrieval system 100. The sample retrieval system 100 includes accumulator 102, sensor chamber 114, and ejector 140. A gas sensor array 200 and thermodynamic sensor array 280 are located within the sensor chamber 114. The sample stream 14 is drawn from the accumulator 102 into the sensor chamber 114, exposing the gas sensor array 200 and the thermodynamic sensor array 280 to the sample stream 14. The sample stream 14 then passes into the ejector 140.

A compressed air source 30 provides compressed air 32 to the ejector 140, creating a pressure drop within the ejector 140 which draws the sample stream 14 through and sensor chamber 114 and into the ejector 140. The compressed air 32 and sample stream 14 are mixed within the ejector 140 and exhausted to atmosphere as the mixture 36. The sample retrieval system 100 is integrated with a remote calibration system 300, which is arranged to inject a small quantity of the gas being measured into the sample stream to enable automated calibration of the gas sensors.

In addition, control and communication system 400 is provided to process the sensor outputs and perform control and communication functions for the fugitive emission sensing system 10. The control and communication system 400 includes sensor interface circuit 402, microcontroller 404, memory 406, communication interface circuit 800, and power conversion circuit 900.

The gas sensor array 200 and thermodynamic sensor array 280 are connected to sensor interface circuit 402, which processes the signals from the sensor arrays and provides the processed signals to microcontroller 404. The microcontroller 404 stores the data from the sensors in memory 406, and may use the sensor data received from the fugitive emission sensing system 10 to initiate control actions to reduce or eliminate the emissions. For example, the microcontroller 404 could close a valve upstream from the emissions source 12 to stop the flow of fluid through the emissions source 12 in order to stop emissions caused by leakage of the fluid. Alternatively, the microcontroller 404 could alter the operating condition of the emissions source 12 itself to reduce or eliminate the fugitive emissions. Microcontroller 404 may use communication interface circuit 800 to provide these control signals to the upstream valve, the emissions source 12, or any other plant equipment that may be used to reduce or eliminate the emissions.

Microcontroller 404 may also use communication interface circuit 800 to provide sensor data to a remote plant process control system 40. The fugitive emission sensing system 10 may perform measurements of fugitive emissions and immediately communicate the resulting sensor data to a separate plant control system 40. Alternatively, the fugitive emission sensing system 10 may store sensor data from each measurement for later retrieval by the plant control system 40.

The communication interface circuit 800 also may receive data and control commands from the plant control system 40. The plant control system 40 may use the sensor data received from the fugitive emission sensing system 10 to initiate control actions to reduce or eliminate the emissions. For example, the plant control system 40 could close an valve upstream or alter the operating condition of the emissions source 12 as described above to reduce or eliminate the fugitive emissions.

The power conversion circuit 900 receives electrical power, which may be transmitted over the communication link with the plant control system 40, and provides power to the communication and control system 400 at a suitable voltage.

The fugitive emission sensing system 10 may be used to detect the presence or measure the concentration of various types of fluids emitted from the emission source 12. The system may be used to detect hazardous, toxic, or polluting substances emitted from the source, or to detect leakage of non-hazardous substances the loss of which may be a cause of concern. The fugitive emission sensing system may be used to detect emissions from any kind of source, particularly industrial process equipment from which hazardous substances may leak. Examples include control valves, block valves, or pumps installed on lines carrying hazardous gases; agitators, screw conveyors, or other equipment installed on process vessels containing hazardous fluids, heat exchangers, reactors, etc. When emissions are detected by the fugitive emission sensing system 10, this data may be used by the fugitive emission sensing system 10 to control the process in such a way as to reduce or eliminate the emissions. Alternatively, the data may be transmitted to a remote plant process control system 40 which may respond by controlling the process in such a way as to reduce or eliminate the emissions.

B. SAMPLE RETRIEVAL SYSTEM

Figure 2:
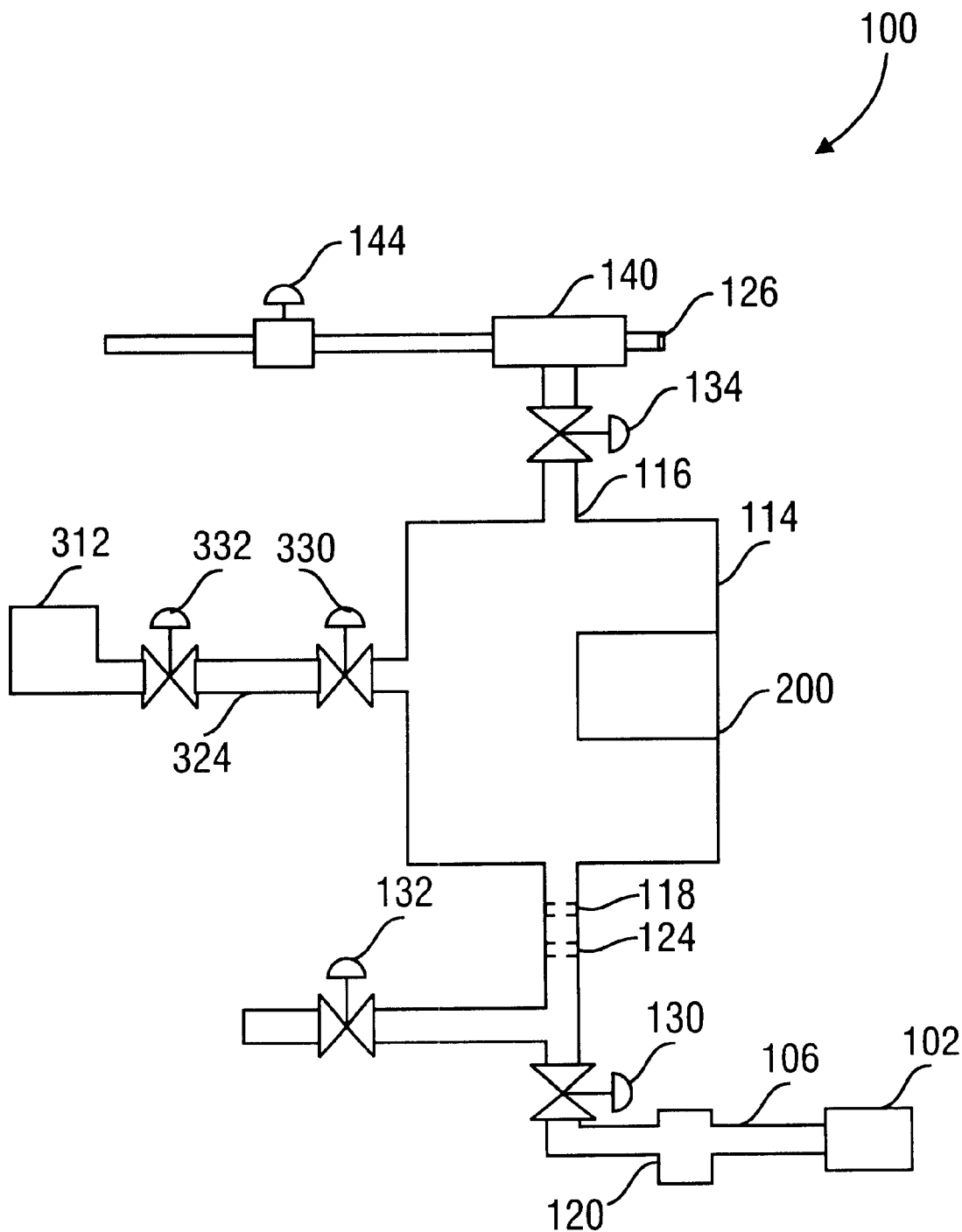
FIG. 2 is a diagram of a sample retrieval system according to an embodiment of the present invention.

Turning now to FIG. 2, a diagram is shown of the sample retrieval system 100 for use in the fugitive emission sensing system of FIG. 1. The sample retrieval system 100 comprises an accumulator 102, retrieval manifold 106, sensor chamber 114, and ejector 140. The accumulator 102 is situated adjacent to the emission source 12 from which an emission is anticipated. The manifold 106 is connected at one end to the accumulator 102 and at the other end to the sensor chamber 114, and permits a sample stream to flow from the emission source into the sensor chamber 114. The manifold 106 is preferably constructed of S31600 stainless steel tubing or other suitable corrosion resistant material.

The sensor chamber 114 contains the gas sensor array 200, and may also contain a thermodynamic sensor array (not shown). The outlet 116 of the sensor chamber 114 is the inlet to the ejector 140. A pneumatic restriction is provided by a restriction orifice 118 at the inlet to the sensor chamber 114. The restriction orifice 118 induces a pressure drop in the sensor chamber to assist in the operation of the ejector 140. The restriction orifice 118 may be constructed from sapphire, stainless steel, or other suitable material which is inert to the emissions expected from the equipment being monitored.

A particulate filter 120 is located along retrieval manifold 106 to collect any particles entrained in the sample stream. Flame path restrictors 124 and 126 are provided at the inlet to the sensor chamber 114 and outlet from ejector 140. Microvalves 130, 132, and 134 are located at various positions to provide for isolation of various parts of the sample retrieval system. Microvalve 130 may be used to isolate the accumulator 102 from the sensor chamber 114. Microvalve 132 provides the ability to draw ambient air into the sensor chamber 114, permitting a base line calibration to be performed on the gas sensors by closing microvalve 130 and opening microvalves 132 and 134.

A remote calibrator may be connected to the sample retrieval system to enable the gas sensors to be calibrated without removing them from the sensor chamber 114. The remote calibrator analyte cell 312 containing calibrant is connected through first microvalve 332 to a dosing chamber 324. The dosing chamber 324 is connected through second microvalve 330 to sensor chamber 114.

The sensor chamber 114 is preferably constructed of cast aluminum. The interior of the chamber may be left unfinished, or coated or machined to achieve a smooth finish to reduce surface sorption of gases from the sample stream. The sensor chamber 114 may be constructed of other suitable corrosion resistant materials that are not affected by the emissions being monitored. The sensor chamber 114 is preferably constructed as a modular unit to permit replacement of the unit in the field.

Figure 3A:
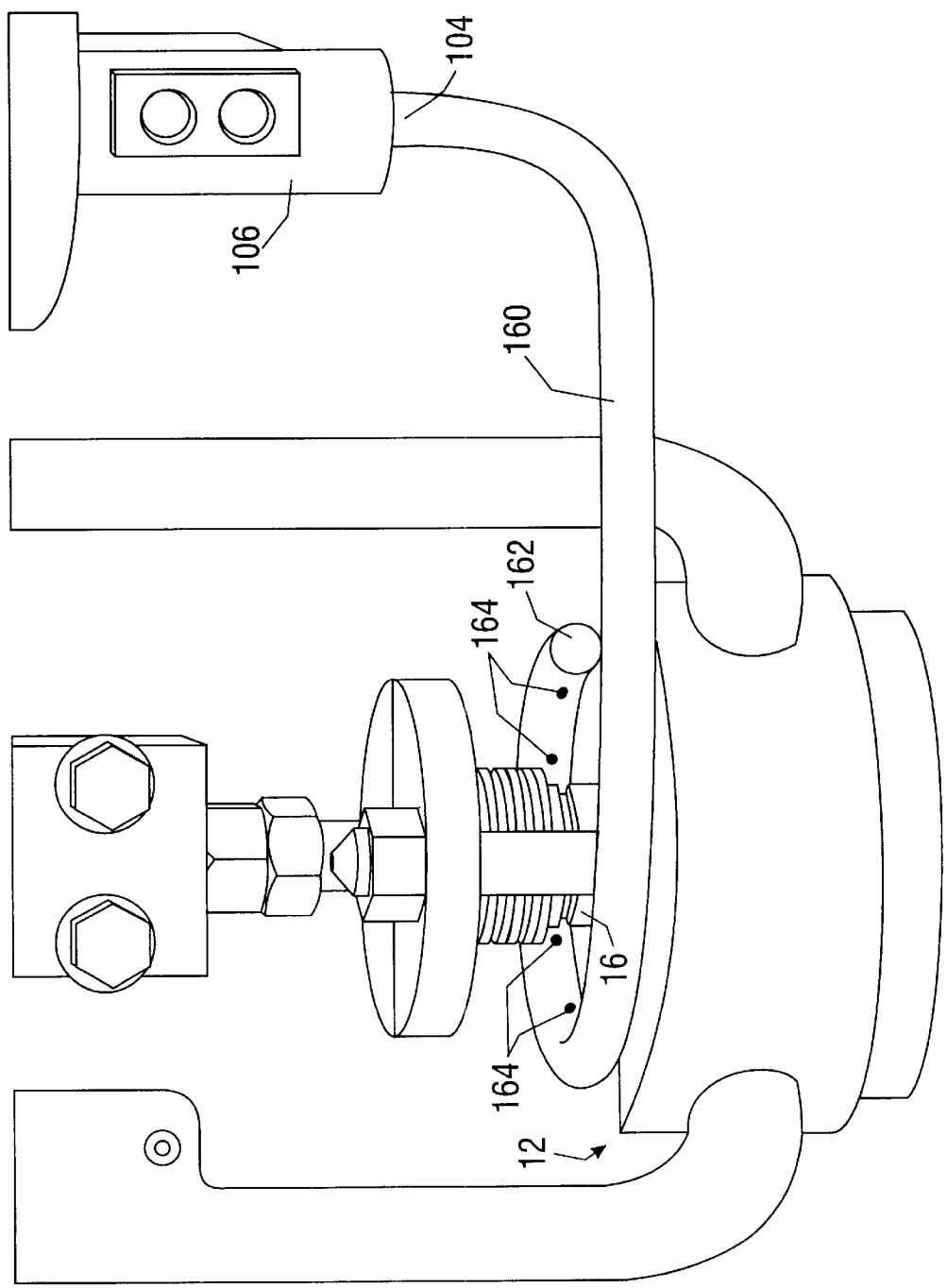
FIG. 3A is a perspective view of a collecting tube in accordance with an embodiment of the invention.

FIG. 3A illustrates one embodiment of the accumulator 102 shown mounted on an emission source 12, depicted in the drawing as a control valve, in which the accumulator 102 comprises a collecting tube 160. The collecting tube 160 facilitates mounting on various types of valve actuators and comprises a single piece of tubing. S31600 stainless steel is an example of a suitable material for the collecting tube 160. The collecting tube 160 may be configured so as to collect gas leaking from the valve stem packing 16 located between the valve bonnet and valve stem. In the embodiment illustrated in FIG. 3A, the collecting tube 160 circumferentially encloses the valve stem packing 16. A first end 162 of the collecting tube 160 is plugged or swagged closed, and the opposite end defines an outlet 104 that interfaces with the intake manifold 106.

The collecting tube 160 defines at least one collecting orifice 164 on the side of the collecting tube 160 facing the emissions source 12. In a particular embodiment, the collecting tube 160 defines seven collecting orifices 164, with the diameters of the collecting orifices 164 generally increasing as the position of the orifice increases from the first end 162 of the collecting tube 160. For instance, the collecting orifice 164 closest to the first end 162 may have a diameter of 0.156 inches, with subsequent collecting orifices 164 having diameters of 0.156, 0.0313, 0.0313, 0.0469, 0.0469, and 0.0625 inches, respectively. The decreasing fluidic resistance facilitates equal collection around the valve packing 16 circumference, carrying fugitive emissions emitted from the emission source 12 into the retrieval manifold 106 and on into the sensing chamber.

Figure 3B:
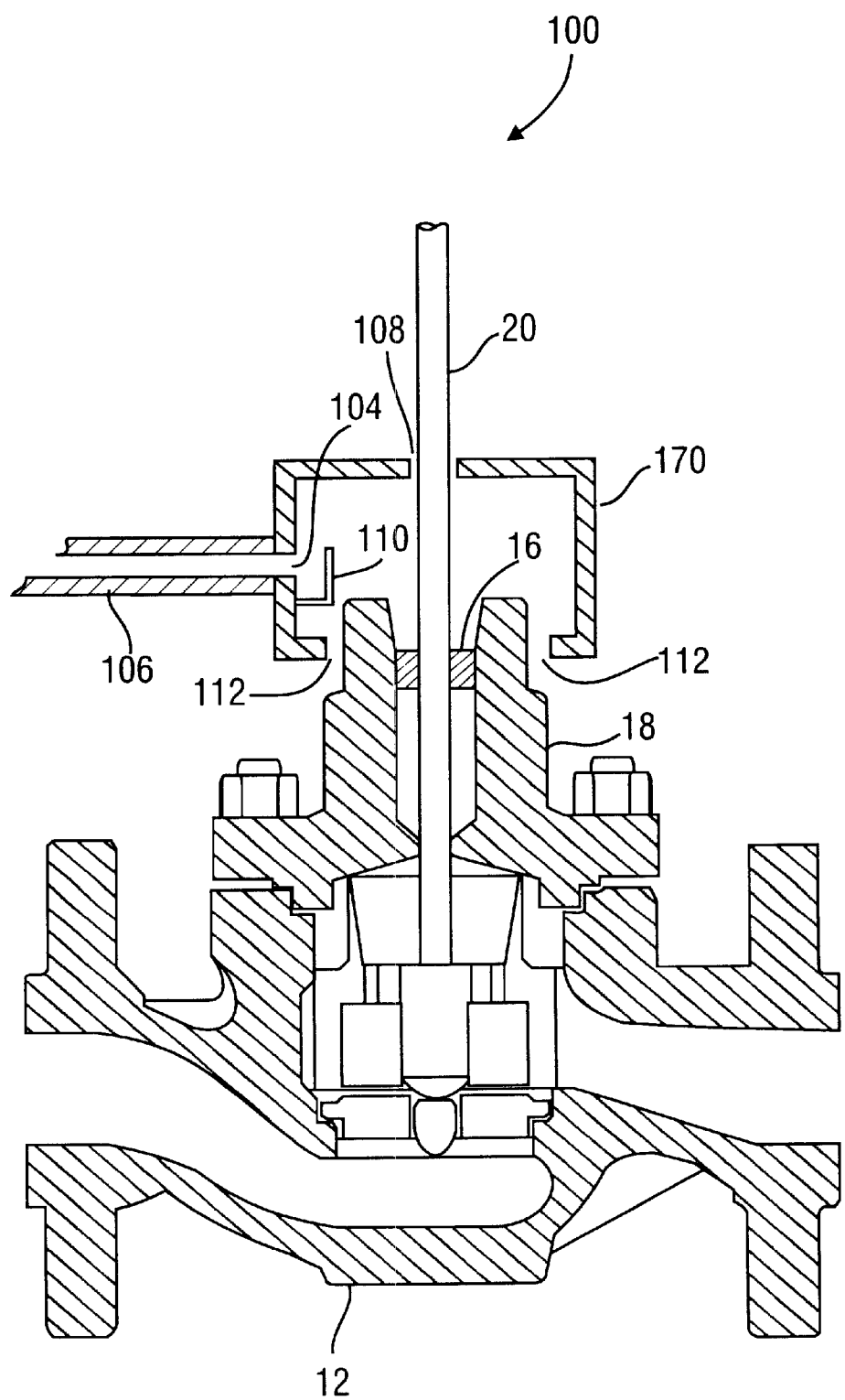
FIG. 3B is a sectional view showing details of a bonnet capsule in accordance with another embodiment of the present invention.

FIG. 3B illustrates an alternative embodiment of the accumulator 102 in accordance with the present invention, in which the accumulator 102 comprises a bonnet capsule 170. The bonnet capsule 170 is shown mounted on an emission source 12, depicted in the drawing as a control valve. The bonnet capsule 170 includes an outlet 104 to which the retrieval manifold 106 is connected, and may also include an opening 108 to permit installation of the bonnet capsule 170 around a valve stem 20 or other obstructing parts of the emission source. The arrangement of the bonnet capsule 170 shown in FIG. 3B is designed to collect gas leaking from the valve stem packing 16 located between the valve bonnet 18 and valve stem 20. The opening 108 is designed to have a small clearance between the valve stem and the bonnet capsule wall to limit the entry of foreign particles into the bonnet capsule 170. A baffle 110 is positioned inside the bonnet capsule 170 to restrict foreign particles in the bonnet capsule 170 from entering the outlet 104, and thus, the retrieval manifold 106.

The bonnet capsule 170 is mounted on the emission source so that a gap 112 remains between the bonnet capsule 170 and the emission source 12. This creates a low impedance pneumatic restriction, which permits air to flow through gap 112, through the bonnet capsule 170, and into retrieval manifold 106. This air flow carries any fugitive emissions emitted from the emission source 12 into the retrieval manifold 106 and on into the sensing chamber. This continual airflow also prevents fugitive emissions from emission source 12 from accumulating in the bonnet capsule 170. Such an accumulation can result in a false high sensor reading due to the integration effect of an accumulation of fugitive emissions.

The bonnet capsule 170 may be constructed of two or more pieces to facilitate installation in situations where the bonnet capsule 170 must be installed around obstructing members. Thus, a bonnet capsule 170 as shown in FIG. 3B, comprising an enclosure split vertically into two halves, may be installed around the valve stem 20 without removing a valve actuator mounted at the top of the valve stem (not shown in FIG. 3B). The bonnet capsule 170 is preferably constructed of S31600 stainless steel or other suitable corrosion resistant material.

Figure 4:
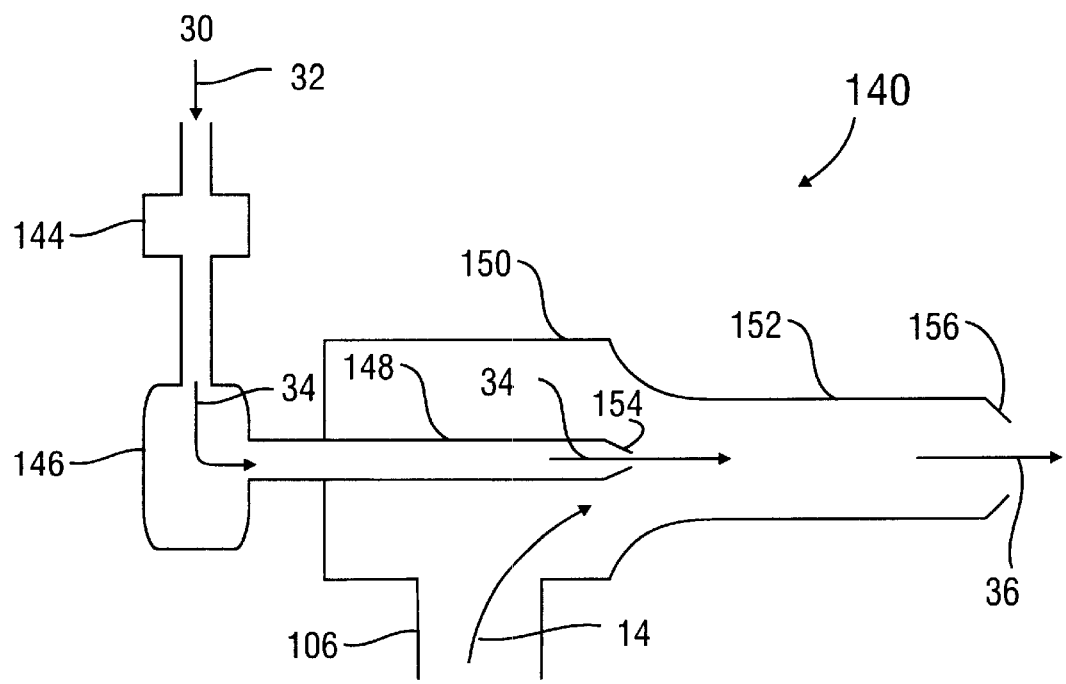
FIG. 4 is a sectional view showing details of the ejector of the sample retrieval system of FIG. 2.

FIG. 4 is a sectional view showing details of the ejector 140 of the sample retrieval system 100 of FIG. 2. The ejector 140 may be integral to the sensor chamber 114 or may be constructed as a separate unit. A compressed air source 30 provides compressed air 32 to a microregulator 144 which provides regulated compressed air 34 to the ejector 140. The compressed air is used to provide the motive power to draw the sample stream 14 from the accumulator 102, through the sensor chamber 114, and into the ejector 140. The compressed air source 30 may be the instrument air supply typically used in process plants to modulate pneumatic control valves or operate pneumatic instruments, although other sources of pressurized gas or liquid may be used. The microregulator 144 is a small pressure regulator of a type commonly used in industrial applications. The microregulator 144 reduces and regulates the pressure of the compressed air to control the flow of the sample stream 14 and minimize the consumption of compressed air 32.

A primary chamber 146 receives regulated compressed air 34 from the microregulator 144 and discharges air into a primary nozzle 148. The primary nozzle 148 is tubular in shape, with an orifice 154 discharging into the throat of the secondary nozzle 152. A secondary chamber 150 is connected to manifold 106 and to the throat of secondary nozzle 152. The secondary nozzle 152 is tubular in shape, with a larger cross-sectional area than the primary nozzle 148, and an orifice 156 discharges to atmosphere.

In operation, the regulated compressed air 34 enters the primary chamber 146 and flows into the primary nozzle 148. The regulated compressed air 34 increases in velocity as it enters the constricted region at the outlet of the primary nozzle 148. This high velocity stream of compressed air discharges into the secondary nozzle 152, entraining air from the secondary chamber 150 and creating a pressure drop in the secondary chamber 150. This pressure drop induces the flow of sample stream 14 from the accumulator 102, through the retrieval manifold 106, and into the secondary chamber 150. Sample stream 14 carries any fugitive emissions from the emission source 12 through the sample retrieval system, exposing the gas sensor array 200 and thermodynamic sensor array 280 to the emissions. The regulated compressed air 34 and the sample stream 14 are mixed together in the secondary nozzle 152 and the mixture 36 is exhausted to atmosphere.

The ejector 140 may be made of stainless steel, or other corrosion resistant material. The primary orifice 154 and secondary orifice 156 are preferably constructed of sapphire.

The ejector 140 is designed to produce a sample stream 14 of known mass flow through the sample retrieval system 100. The flow rate of the sample stream 14 is determined by the diameters of the primary orifice 154, secondary orifice 156, sensor chamber inlet orifice 118, and the pressure of regulated compressed air 34. The sample retrieval system 100 operates satisfactorily at a sample stream flow rate of about 0.425 square cubic feet per hour. This flow rate may be achieved with a primary orifice diameter of 0.011 inches, secondary orifice diameter of 0.024 inches, sensor chamber inlet orifice diameter of 0.013 inches, and regulated compressed air pressure of about 3.0 pounds per square inch gauge. However, different dimensions and operating conditions for the ejector 140 may be required to effectively collect emissions from different types of emissions sources.

By controlling the pressure of the regulated compressed air 34 into the ejector 140, the pressure drop within the secondary chamber 150 can be controlled, and thus the velocity of the sample stream 14 through the retrieval manifold 106 and sensor chamber 114 can be controlled. Furthermore, the mass flow of the sample stream 14 can be calculated given the geometry of the ejector 140, retrieval manifold 106 and sensor chamber 114, and the pressure of the compressed air at the inlet to the primary chamber 146.

The design of the sample retrieval system 100 thus eliminates the need for a mass flow sensor to measure the sample stream flow through the retrieval manifold 106. The system described also eliminates the need for pumps or fans located near the emission source to collect the sample stream, resulting in a simple and inexpensive design. Lastly, the sample retrieval system can be designed to conform to EPA sample collection requirements.

C. SENSOR ARRAY

1. Overview

Figure 5:
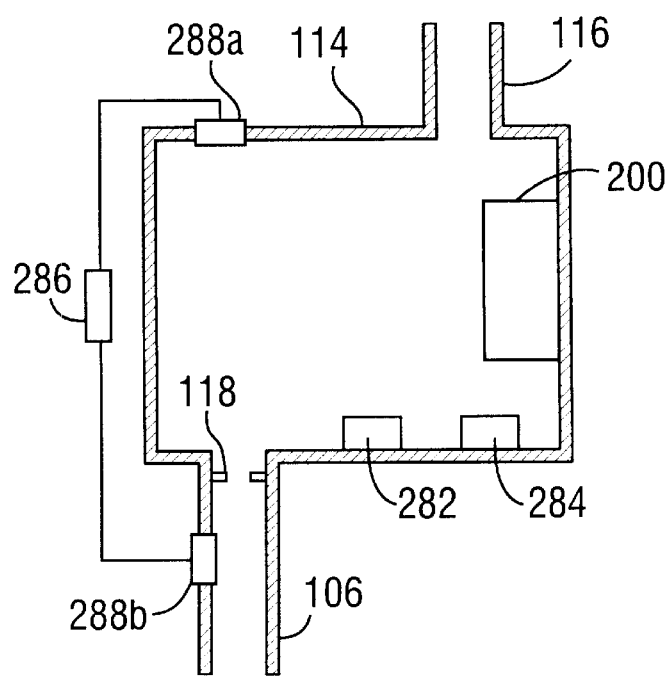
FIG. 5 is a sectional view showing the arrangement of sensors in the fugitive emission sensing system of FIG. 1.

FIG. 5 is a sectional view showing the arrangement of sensors in the sensor chamber 114 of the fugitive emission sensing system 10 of FIG. 1. The sensor chamber 114 is shown with an inlet from the retrieval manifold 106 and outlet 116 to the ejector 140 (not shown). An inlet orifice 118 is positioned at the inlet to sensor chamber 114. A gas sensor array 200 and an array of thermodynamic sensors are located in sensor chamber 114.

The gas sensor array 200 comprises one or more sensors responsive to the particular fugitive emission being monitored. In the embodiment shown in FIG. 5, the gas sensor array 200 comprises one or more quartz crystal microbalance (QCM) gas sensors 210 (shown in FIG. 6 and described further below). The gas sensor array 200 is incorporated into an assembly that fits within the sensor chamber 114 and can be conveniently removed and replaced in the field.

2. Quartz Crystal Microbalance Gas Sensors

Figure 6:
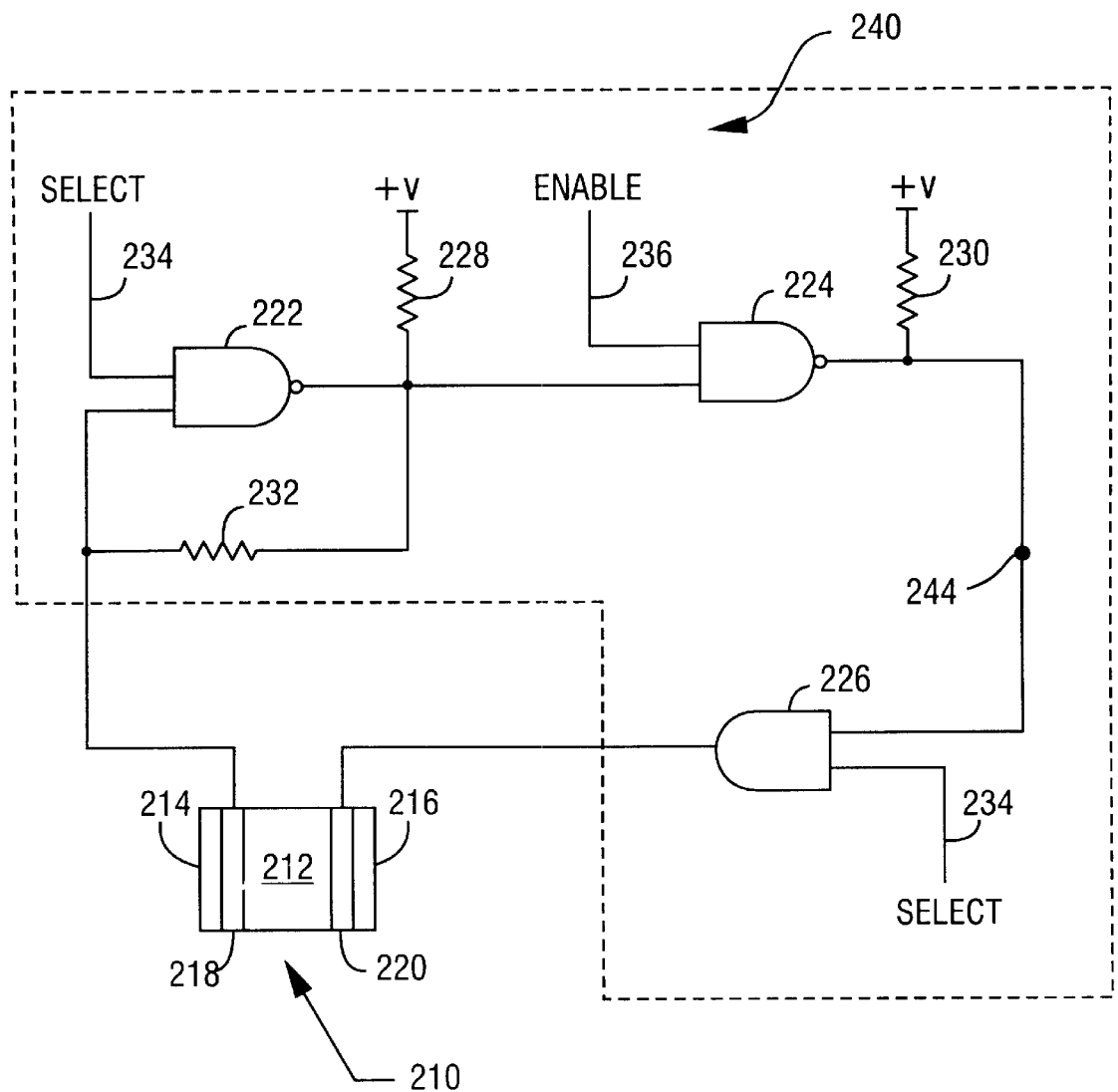
FIG. 6 is a schematic of a Quartz Crystal Microbalance (QCM) oscillator for use in a fugitive emission sensing system in accordance with the present invention.

FIG. 6 shows a quartz crystal microbalance (QCM) circuit comprising a QCM gas sensor 210, which may be included in the gas sensor array 200, and oscillator circuit 240. The QCM gas sensor 210 comprises a quartz crystal substrate 212, polymer coatings 214 and 216, and electrodes 218 and 220 located between the substrate and the coatings. The oscillator circuit 240 comprises NAND gates 222 and 224, and AND gate 226, connected in series. Resistor 228 is connected between the output of NAND gate 222 and circuit power supply voltage +V, and resistor 230 is connected between the output of NAND gate 224 and circuit power supply voltage +V. Resistor 232 is connected across NAND gate 222, connecting a first input to the output. A select signal 234 is connected to the second input of NAND gate 222, and the same select signal is also connected to an input of AND gate 226. An enable signal 236 is connected to an input of NAND gate 224.

When the select signal 234 and enable signal 236 are both high, NAND gate 222 and 224 act as high-gain inverting amplifiers and cause oscillator output 244 to oscillate between high and low voltage, producing an oscillating square wave output. The oscillating voltage from the oscillator output 244 is transferred through AND gate 226 and applied across the crystal substrate 212, exerting a physical stress on the crystal due to the piezoelectric effect and causing the QCM gas sensor 210 to physically resonate. The resonating crystal interacts with the oscillating circuit causing the oscillating circuit to oscillate at the resonant frequency of the QCM gas sensor 210. Thus, the frequency of oscillator output 244 will vary as the resonant frequency of the QCM gas sensor 210 varies.

AND gate 226 provides isolation between the oscillator circuit 240 and the QCM gas sensor 210 when the sensor is not selected. The output from NAND gate 224 is connected to a first input of AND gate 226, the second input being connected to select signal 234. When the QCM gas sensor 210 is selected for measurement, select signal 234 is high and the output from AND gate 226 follows any change of state present at its first input. Thus, the oscillating output from NAND gate 224 will be transferred to terminal 220 of quartz crystal substrate 212 and the QCM gas sensor 210 will be connected into the oscillator circuit 240. When the QCM gas sensor 210 is not selected for measurement, select signal 234 is low and the output from AND gate 226 will be low regardless of the signal at the first input of AND gate 226. This will result in the QCM gas sensor 210 being isolated from oscillator circuit 240.

The resonant frequency of the QCM gas sensor 210 is a function of the size, shape, and cut of the quartz crystal substrate 212. Quartz crystal exhibits a natural resonant frequency that is a function of the mass and structure of the crystal. The precise size, type of cut, and thickness of the quartz crystal substrate 212 are selected to result in a particular resonant frequency. An AT-cut crystal with a nominal resonant frequency of 9 MHz is suitable for gas sensor applications. Suitable quartz crystal substrates may be obtained from Standard Crystal Corporation of California. Other types of piezoelectric acoustic wave devices may also be used in place of the QCM gas sensor, including surface acoustic wave (SAW) devices, acoustic plate mode (APM) devices, or flexural plate wave (FPW) devices. However, these alternative devices may have higher operating frequencies of over 100 MHz, and alternative operating modes, necessitating the use of circuitry capable of measuring such high frequencies. The electrodes 218 and 220 may be constructed of gold-on-chromium, although other suitable corrosion resistant conductors may be used.

The resonant frequency of the QCM gas sensor 210 is a function of the total mass of the device. The mass of the polymer coating 214 and 216 affects the total mass of the device, and thereby affects the resonant frequency of the QCM gas sensor 210. When gas molecules are sorbed into or deposited onto the polymer coating 214 and 216, the mass of the polymer coatings is slightly increased, and the resonant frequency of the QCM gas sensor 210 changes. The resonant frequency of QCM gas sensor 210 is also a function of the viscoelectric properties of the coatings, and mechanical stresses caused by temperature effects and the QCM mounting arrangement. However, these effects are either negligible or can be compensated for, allowing the QCM gas sensor 210 of the present invention to function principally as a mass sensor. Thus, a very sensitive gas detector may be constructed by selecting a polymer coating that has a chemical affinity with a particular gas or class of gases of interest.

When the gas of interest comes in contact with the QCM gas sensor 210, gas molecules are absorbed and deposited onto the polymer coating 214 and 216 through various sorption processes. The sorption of gas molecules increases the mass of the QCM gas sensor 210, thereby altering its resonant frequency and causing a corresponding change in the operating frequency of oscillator 230. The quantity of gas molecules absorbed and deposited, and the resulting change in the operating frequency of oscillator 230, is a function of the concentration of the gas being measured in the environment surrounding the QCM gas sensor 210. The frequency changes linearly with change in gas concentration, within certain limits. Some variation in the resonant frequency of the quartz crystal substrate 212 also will occur due to aging of the crystal and temperature effects.

Thus, a change in concentration of the gas of interest may be measured by measuring the change in frequency of oscillator output 244. The gas sensor may be calibrated by exposing the QCM gas sensor 210 to known concentrations of gas and recording the resulting frequency of oscillator output 244. The gas sensor may then be used to measure the absolute concentration of a gas. The gas sensor of FIG. 1 may be designed to detect very low concentrations of gas. However, in order to measure low gas concentrations, a means of measuring small variations in frequency of the oscillator output 244 is required. A QCM gas sensor interface circuit in the communication and control system 400 is described below to make these measurements.

Figure 7:
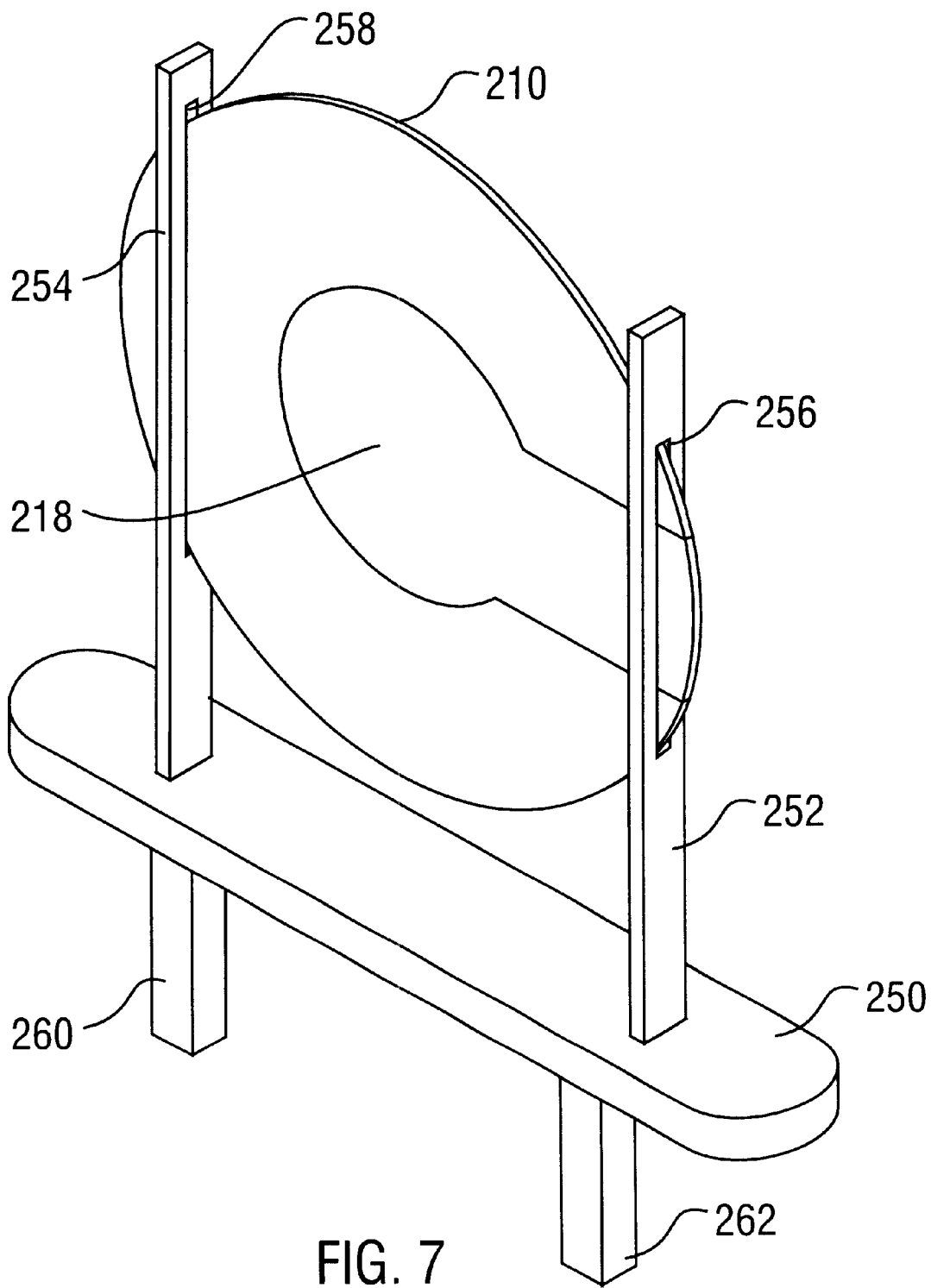
FIG. 7 is a diagram showing mounting details for the QCM gas sensor of FIG. 5.

The QCM gas sensor 210 is sensitive to vibration and to the flow characteristics of the gas sample stream 14. Such vibration may be caused by the operation of pumps, motors, or other equipment which is connected to the valve on which the fugitive emission sensing system 10 is mounted. The mounting arrangement for the QCM gas sensor 210, illustrated in FIG. 7, is designed to isolate the sensor from these vibrations.

A base 250 supports two rigid support members 252 and 254, each having a slit opening (256 and 258). The QCM gas sensor 210 is formed in the shape of a flat disk, and is positioned between the rigid support members 252 and 254 so that the periphery of the sensor disk protrudes through the slits 256 and 258 in the support members. Electrode 218 of the QCM gas sensor 210 has a circular portion in the center of the sensor disk and an elongated portion extending outwards to the support member 252 and through the slit 256, where electrode 218 and support member 252 make electrical contact. The support member 252 is electrically connected to electrical terminal 262, thus completing an electrical path between electrode 218 and electrical terminal 262. Electrode 220 (not shown) is located on the opposite side of the sensor disk and shaped similarly to electrode 218. However, the elongated portion of electrode 220 extends towards support member 254 and through slit 258, completing an electrical path from electrode 220, support member 254, and electrical terminal 260. Electrical terminals 260 and 262 connect the QCM gas sensor 210 into the oscillator circuit 240 shown in FIG. 6.

The QCM gas sensors are preferably mounted in a removable module to facilitate replacement and maintenance of the sensor array. The QCM gas sensors are densely packed to reduce the effect of any gradient in the concentration of the fugitive emission within the sensor chamber. Multiple QCM gas sensors 210 may be used with each sensor having a different polymer coating, permitting discrimination between a variety of different fugitive emissions.

3. Thermodynamic Sensors

The thermodynamic sensor array comprises one or more sensors responsive to the thermodynamic conditions in the sensor chamber 114. In the embodiment shown in FIG. 5, the thermodynamic sensor array comprises a temperature sensor 282, a relative humidity sensor 284, and a differential pressure sensor 286.

The QCM gas sensors are sensitive to variations in temperature. Measurement of the temperature in the sensor chamber 114 may be used to compensate for gas sensor measurements affected by temperature variation. Temperature sensor 282 is located within the sensor chamber 114, and may optionally be located in the same removable assembly as the gas sensor array 200. A QCM sensor without any polymer coating may be used as the temperature sensor 282. The uncoated QCM sensor is constructed similarly to the QCM gas sensor 210 described above, having a quartz crystal substrate and being connected to an oscillator circuit, but lacking any polymer coating. The QCM temperature sensor 282 is hermetically sealed to prevent absorption of fluid from the sample stream 14 or ambient air. Any variation in the temperature of the quartz crystal substrate of the sensor will result in a corresponding change in the resonant frequency of the uncoated QCM temperature sensor 282. As with the QCM gas sensor 210, some variation in the resonant frequency of the quartz crystal substrate also will occur with aging of the device. As an alternative to the use of a QCM device, a resistance temperature detector or other common type of temperature sensor also may be used.

Relative humidity affects the measurements made by gas sensor array 200 because the water molecules within the sample stream 14 compete with the molecules of the fugitive emission being measured for sorption by the polymer surfaces of the QCM gas sensor 210. Relative humidity sensor 284 is located in the sensor chamber 114. A QCM sensor similar to the QCM gas sensor 210 may also be used for the relative humidity sensor 284. When used as the relative humidity sensor 284, the polymer coating applied to the quartz crystal substrate of the QCM sensor is selected to be hydrophilic. The resonant frequency of the QCM relative humidity sensor 284 varies with the amount of water deposited on the polymer coating on the surface of the sensor.

The differential pressure sensor 286 measures the flow of the sample stream 14 through the sensor chamber 114. Pressure taps 288a and 288b measure the pressure in the retrieval manifold 106 and sensor chamber 114 respectively, thus measuring the pressure drop across orifice 118 at the inlet to the sensor chamber 114. The flow of gas into the sensor chamber 114 can be calculated from the differential pressure measurement using well known techniques.

D. REMOTE CALIBRATOR SYSTEM

Figure 8:
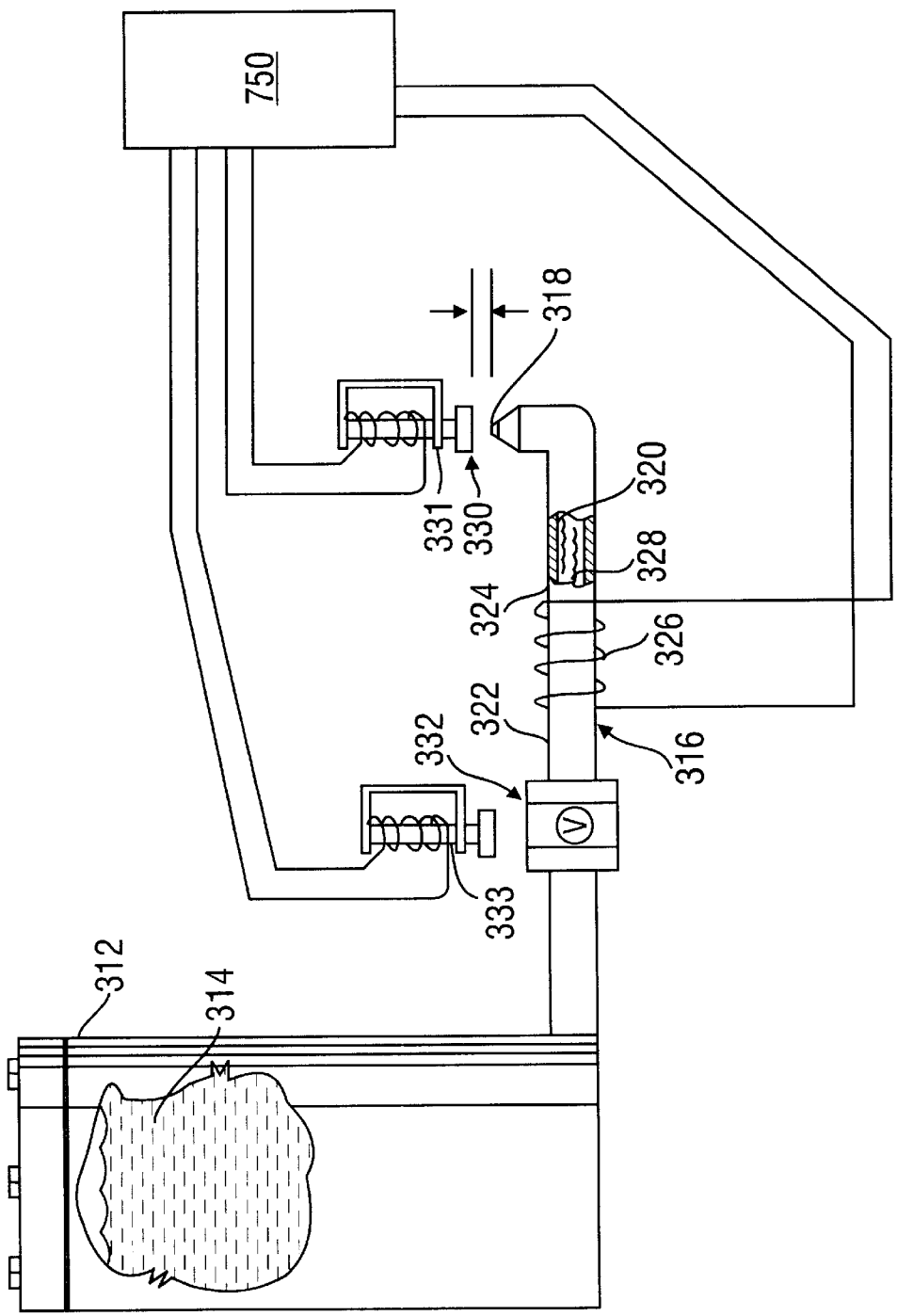
FIG. 8 is a schematic view, partly in section, of a remote calibrator system for use in the fugitive emission sensing system of FIG. 1.

QCM gas sensors typically degrade due to the effects of aging, temperature, humidity, poisoning, and oxidation on the polymer coating. Periodic calibration of the gas sensors permits the fugitive emission sensing system to compensate for these effects. To permit efficient and consistent calibration of the gas sensors, the fugitive emissions sensing system includes a remote calibrator. FIG. 8 is a sectional view of an embodiment of a remote calibrator system for use in the fugitive emission sensing system of FIG. 1.

The calibration technique selected for use with the fugitive emissions sensing system provides for exposing the gas sensor array 200 to the same type of emissions that the system is designed to measure. By exposing the sensors to known quantities of the emissions, the analysis of the resulting data from the sensors is reduced to a regression problem. The gas sensor array 200 is exposed to the process plant atmosphere containing three increasingly greater concentrations of the emission of interest. The three calibration points are chosen to encompass the entire operational range of the sensor (from the lowest concentration of the emission of interest to the highest concentration) and define the sensor's performance for a specific measurement interval. The frequency of measurement may be as often as daily with measurement times not to exceed 10 minutes. Power consumption is a critical parameter in all aspects of the system and drives many aspects of the design.

FIG. 8 shows a remote calibrator 300 for performing automatic calibration of the gas sensors use with the fugitive emission sensing system 10. The remote calibrator 300 is mounted in the field adjacent to the gas sensors. Remote calibrator 300 includes a reservoir 312 which contains a quantity of liquid analyte calibrant 314, which is preferably the same material as is running through the valve to the monitored.

Remote calibrator 300 includes a conduit 316 which extends between the reservoir 312 and an outlet nozzle 318. Conduit 316 includes a bore 320 extending therethrough, and further includes an intermediate or central portion 322, a portion of which defines a dosing chamber 324. Dosing chamber 324 is preferably of predetermined volume, which for purposes of the preferred embodiment is in the range of 2 microliters ($2 \times 10^{-6}$ cubic centimeters). Conduit 316 is preferably constructed of stainless steel tubing having an inside diameter of 0.008 inches and an outside diameter of 0.50 inches, or any other suitable thickwall small diameter tubing. A thermal activator 326, which is preferably a resistive coil or a radio frequency heating unit, surrounds the conduit 316 adjacent the dosing chamber 324, enabling the activator 326 to heat a measured quantity 328 of calibrant 314 contained within the dosing chamber 324. The thermal activator 326 is preferably capable of bringing the measured quantity 328 contained within the dosing chamber 324 to its boiling point very quickly, as in the range of about 10 milliseconds.

An outlet valve 330 having a magnetically coupled actuator 331 is located at outlet nozzle 318, and is movable between an open position in which the bore 320 and dosing chamber 324 are in flow communication with the surrounding atmosphere, and a closed position in which the bore 320 and dosing chamber 324 are isolated from the surrounding atmosphere. A second valve 332 having a magnetically coupled actuator 333 is disposed along conduit 316 between dosing chamber 324 and reservoir 312. Valve 332 is movable between an open position in which dosing chamber 324 is in flow communication with reservoir 312, and a closed position in which the dosing chamber 324 is isolated from the reservoir 312. Preferably, each of valves 330, 332 are remotely operable from a remote calibrator control circuit 750. Remote calibrator control circuit 750 is also used to energize the thermal activator 326 as will be discussed in greater detail below. Further, the pneumatic impedance through valve 330 is preferably about fifty (50) times greater than the pneumatic impedance through valve 332, the importance of which will be discussed in greater detail below. Valve 330 preferably includes a chemically resistant soft seat, such as VITON or TEFLON. These fluorinated materials prevent calibrant absorption into the seat, thus preventing "off-gassing." The closure force of valve 330 may be relatively low, such as in the range of 25 pounds per square inch of closure force on nozzle 318.

In operation, when the remote calibrator 300 is inactive, valve 330 is closed, valve 332 is open, and the calibrant 314 in reservoir 312 is free to flow into the dosing chamber 324. When it is desired to activate the remote calibrator 300, the remote calibrator control circuit 750 closes valve 332, thus seriously impeding or preventing flow between dosing chamber 324 and reservoir 312, and thermal activator 326 is energized. Simultaneously, or shortly thereafter, valve 330 is opened. The now vaporized calibrant 314 contained within dosing chamber 324 is at boiling point, and is ejected through the open nozzle 318 into the sensor chamber 114 (not shown). At that point, the exhausted calibrant can be mixed with a known quantity of ambient air drawn from around the emissions source 12, for measuring or predicting the leak emissions. The gas sensor array 200 can be calibrated by comparing the obtained sensor reading to empirical data, or by using other known methods.

Alternatively, the impedance between the dosing chamber 324 and the reservoir 312 may be achieved using a mechanical restriction rather than a closeable valve. Also, in less severe environments or in environments where inertial dispersion of calibrant is not expected, it is conceivable that surface tension and pneumatic impedance may be sufficient to prevent evaporation as well as backward flow of the calibrant, thus making it possible to dispense with one or both of the valves.

E. CONTROL AND COMMUNICATIONS SYSTEM

1. Overview

Figure 9:
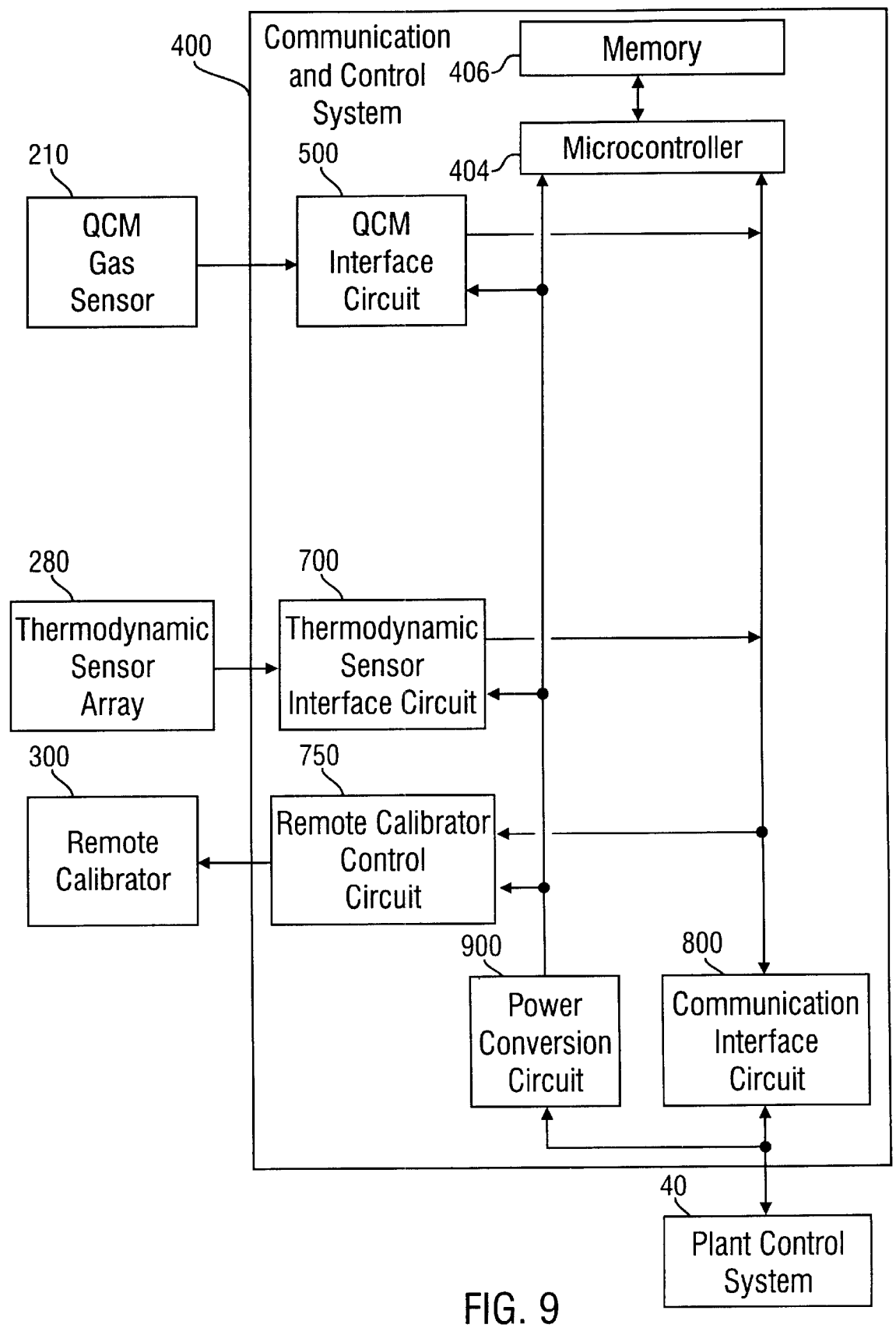
FIG. 9 is a block diagram showing the major components of a control and communications system for use in the fugitive emission sensing system of FIG. 1.

FIG. 9 is a block diagram showing the major components of a control and communications system for use in the fugitive emission sensing system of FIG. 1. The control and communications system 400 includes circuits to interface to the sensors (QCM interface circuit 500 and thermodynamic sensor interface circuit 700) and to control the remote calibrator (remote calibrator control circuit 750). A microcontroller 404 communicates with each of these and sends data to the communication interface circuit 800 for transfer to a plant control system 40. A power conversion circuit 900 provides power to the communication and control system 400.

2. Microcontroller and Memory

The microcontroller 404 controls the operation of the fugitive emission sensing system 10. The microcontroller 404 manages communications between the components of the fugitive emission sensing system 10, and communication with a plant control system 40. The microcontroller 404 also provides storage of measurement data from the gas sensor array 200 and thermodynamic sensor array 280, as well as data derived from calibration of the gas sensors, in memory 406.

The microcontroller 404 may be programmed to perform fugitive emission measurements upon request from the plant control system 40. The data may be stored in memory 406 temporarily and uploaded to the plant control system 40 after each measurement cycle. Alternatively, the microcontroller 404 may be programmed to perform fugitive emission measurements on a set schedule. The measurement data may be stored in non-volatile memory 406 and uploaded only upon request for the data from the plant control system 40.

3. QCM Gas Sensor Interface

Several techniques can be used to determine the resonant frequency of QCM gas sensor 210. One method involves resonant frequency determination based upon impedance measurements. This technique is an analog-digital hybrid circuit that is prone to noise, is complex, and expensive to implement. However, the use of a frequency counter provides a low cost fully digital circuit that has high noise immunity, and simple integration of commercially available components make this technique novel and robust.

Figure 10:
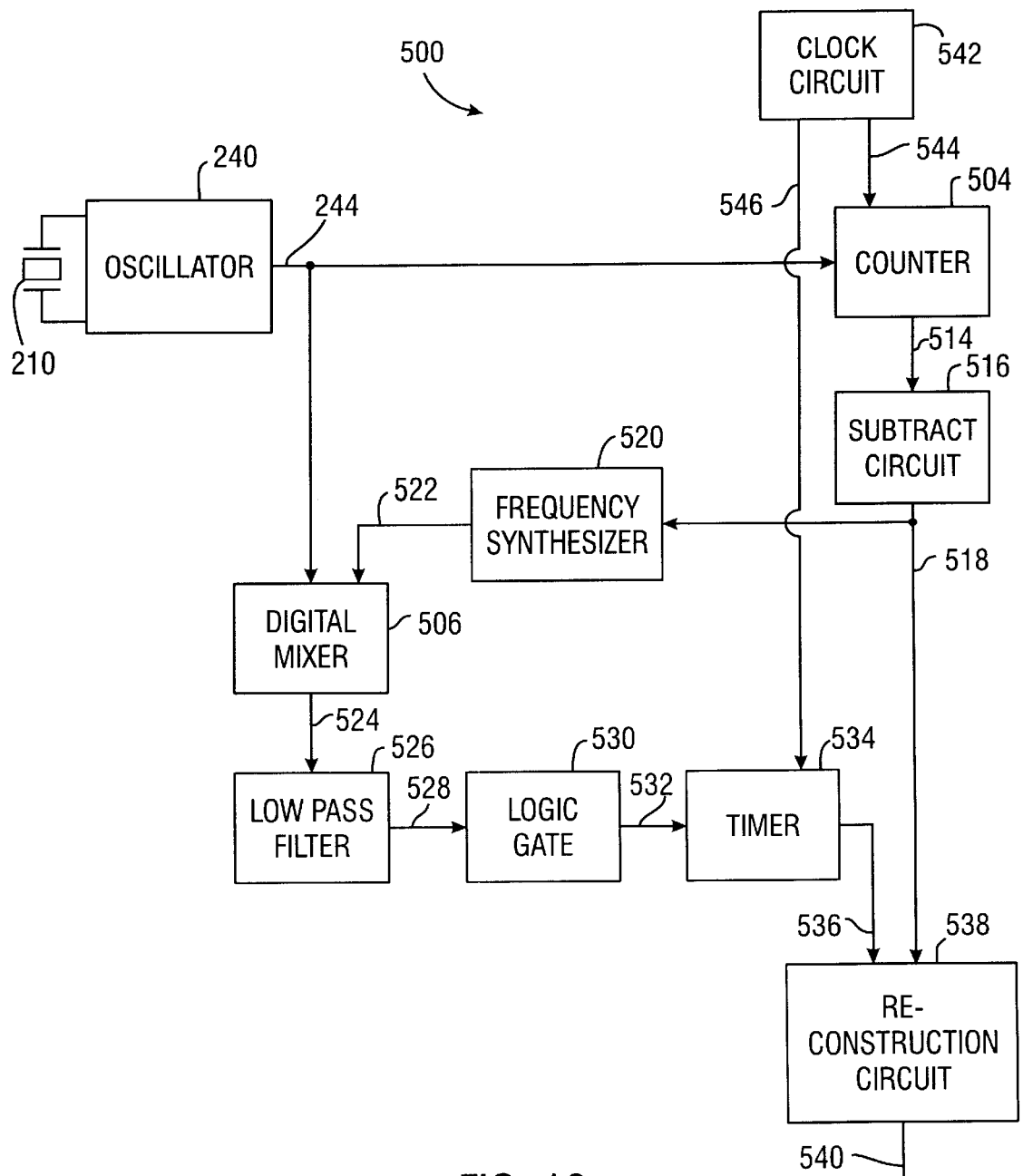
FIG. 10 is a block diagram of a QCM gas sensor interface circuit for use with the QCM gas sensor of FIG. 6.

FIG. 10 is a block diagram of the main functional components of a digital QCM gas sensor interface circuit for use in the control and communications system of FIG. 9. The QCM gas sensor 210 and oscillator 240 are shown, and the oscillator output is connected to counter 504 and a first input of digital mixer 506. The counter 504 is connected to subtract circuit 516, which is used to generate "coarse" measurement 518, as described below. Coarse measurement 518 is an input to digital frequency synthesizer 520, which generates reference frequency 522. Reference frequency 522 is a second input to digital mixer 506. The output of digital mixer 506 is connected to low pass filter 526, whose output is connected to a logic gate 530. The logic gate 530 may be a buffer or inverter, or a Schmitt trigger to provide noise immunity. The logic gate output is connected to timer 534, which is used to generate "fine" measurement 536, as described below. Coarse measurement 518 and fine measurement 536 are inputs to add circuit 538, which generates final measurement 540. Clock circuit 542 generates gate signal 544 which is an input to counter 504 and internal clock frequency 546 which is an input to timer 534.

Initially the output of oscillator 240 is the QCM frequency 502, which has the same frequency as the resonant frequency of QCM gas sensor 210, typically 9 MHz. As mentioned earlier, this frequency will vary as a result of the sorption of gas molecules into and onto the polymer coatings 214 and 216 of the QCM gas sensor 210. The counter 504 counts the number of cycles (measured by the rising edges of low to high transitions) of QCM frequency 502. This count is initial frequency measurement 514. Counter 504 is a 16-bit device so the maximum count possible for the 16-bit initial frequency measurement 514 is $2^{16}$ or 65,536. To prevent an overflow in the 16-bit count, the counter 504 must be enabled for a sufficiently short time such that the total expected count is less than 65,536. To prevent such an overflow, the clock circuit 542 generates a periodic gate signal 544 to enable the counter 504 for a short period. The counter 504 counts the number of cycles of QCM frequency 502 that occur between each gate signal.

The gate period selected is dependent on the frequency of the signal being measured. A longer gate period will provide greater resolution, while a shorter gate period will provide for greater variation in the frequency being measured without causing an overflow. For example, a 9 MHz signal will provide 54,000 counts in a 6 ms gate period. The resolution of the 16-bit count for a 9 MHz signal and a 6 ms gate period is 9 MHz/54,000 counts, or approximately 167 Hz (i.e. each count represents approximately 167 Hz). The actual error is not symmetrical due to truncation of the digital values that occurs during count accumulation. However, to precisely calculate the mass of gas molecules sorbed into the polymer coating of QCM gas sensor 210, greater accuracy is required.

Higher resolution is achieved by digitally mixing the QCM frequency 502 with a reference frequency and measuring the difference frequency between the two signals. The reference frequency is derived from the initial frequency measurement 514 produced by the counter 504. One count is subtracted from the initial measurement 514 by subtract circuit 516, and the resulting "coarse" measurement 518 is an input to the digital frequency synthesizer 520. The digital frequency synthesizer 520 generates a reference signal 522 which has a frequency corresponding to the value of coarse measurement 518. The subtraction of one count to give coarse measurement 518 ensures that the frequency of the reference signal 522 is always less than the frequency of QCM frequency 502. This simplifies reconstruction of the final measurement 540 by eliminating the need to determine whether the output from the digital mixer 506 represents a positive or negative difference in frequency (i.e. whether fine measurement 536 should be added or subtracted from the coarse measurement 518).

Reference signal 522 and QCM frequency 502 are both inputs to digital mixer 506. Digital mixing may be accomplished by performing a Boolean Exclusive OR operation on the two inputs. The digital mixing of the two high frequency signals produces a sinusoidally varying pulse width modulated signal 524. The pulse width modulated signal 524 varies sinusoidally due to the periodic phase variations between the frequencies of the reference signal 522 and QCM frequency 502. The pulses are integrated by a first order low-pass filter 526 to remove the high frequency carrier and passed through a logic gate 530 to provide a square wave difference frequency signal 532. The difference frequency signal 532 is an input to timer 534.

The difference frequency signal 532 has a much lower frequency than the QCM frequency 502, and can be measured very precisely. The timer 534 is configured to count the number of cycles of internal clock signal 546 (measured by the rising edges of low to high transitions) during each cycle of difference frequency signal 532. For an internal clock signal 546 with a frequency of 5 MHz, the internal clock cycle time is 200 nanoseconds. Thus, timer 534 increments its count every 200 nanoseconds during one cycle of difference frequency signal 532.

Coarse measurement 518 has the same resolution as initial measurement 514, approximately 167 Hz. The frequency of reference signal 522 is nominally 167 Hz less than QCM frequency 502, because reference signal 522 is generated from coarse measurement 518 which is one count less than initial frequency measurement 514. Thus, the difference in frequency between reference signal 522 and QCM frequency 502 may theoretically vary from approximately 167 Hz to 333 Hz (the actual difference in frequency will be greater due to truncation errors), and the difference frequency signal 532 will thus vary between 167 Hz and 333 Hz. The timer 534 measures this low frequency difference frequency signal 532 with a resolution of at least 0.1 Hz, to produce "fine" measurement 536.

Finally, the reconstruction circuit 540 adds fine measurement 536 to coarse measurement 518 to produce final measurement 540. Thus, a vernier frequency counter has been developed to accurately determine the operating frequency of the QCM gas sensor 210.

Figure 11:
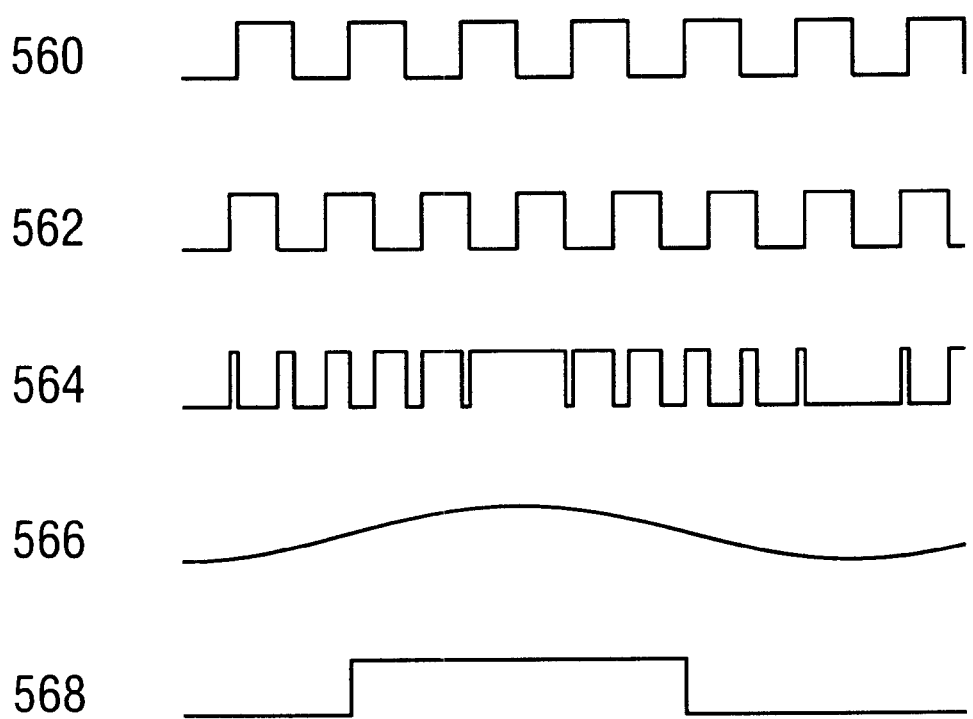
FIG. 11 is a diagram of typical waveforms generated by the QCM gas sensor interface circuit of FIG. 10.
Figure 12A:
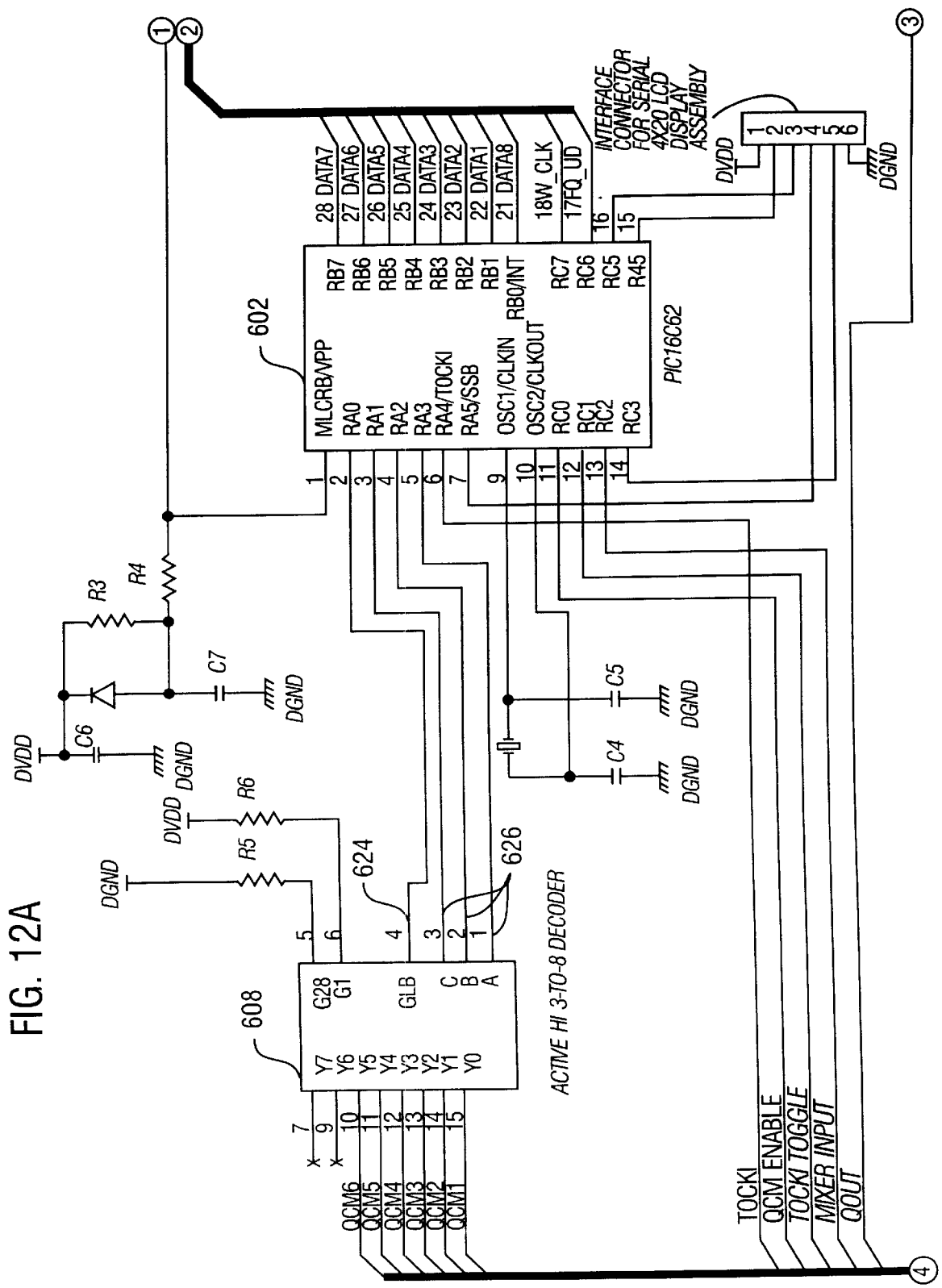
FIGS. 12A–12D show a circuit diagram of a QCM gas sensor interface circuit for use with the QCM gas sensor of FIG. 6.
Figure 12B:
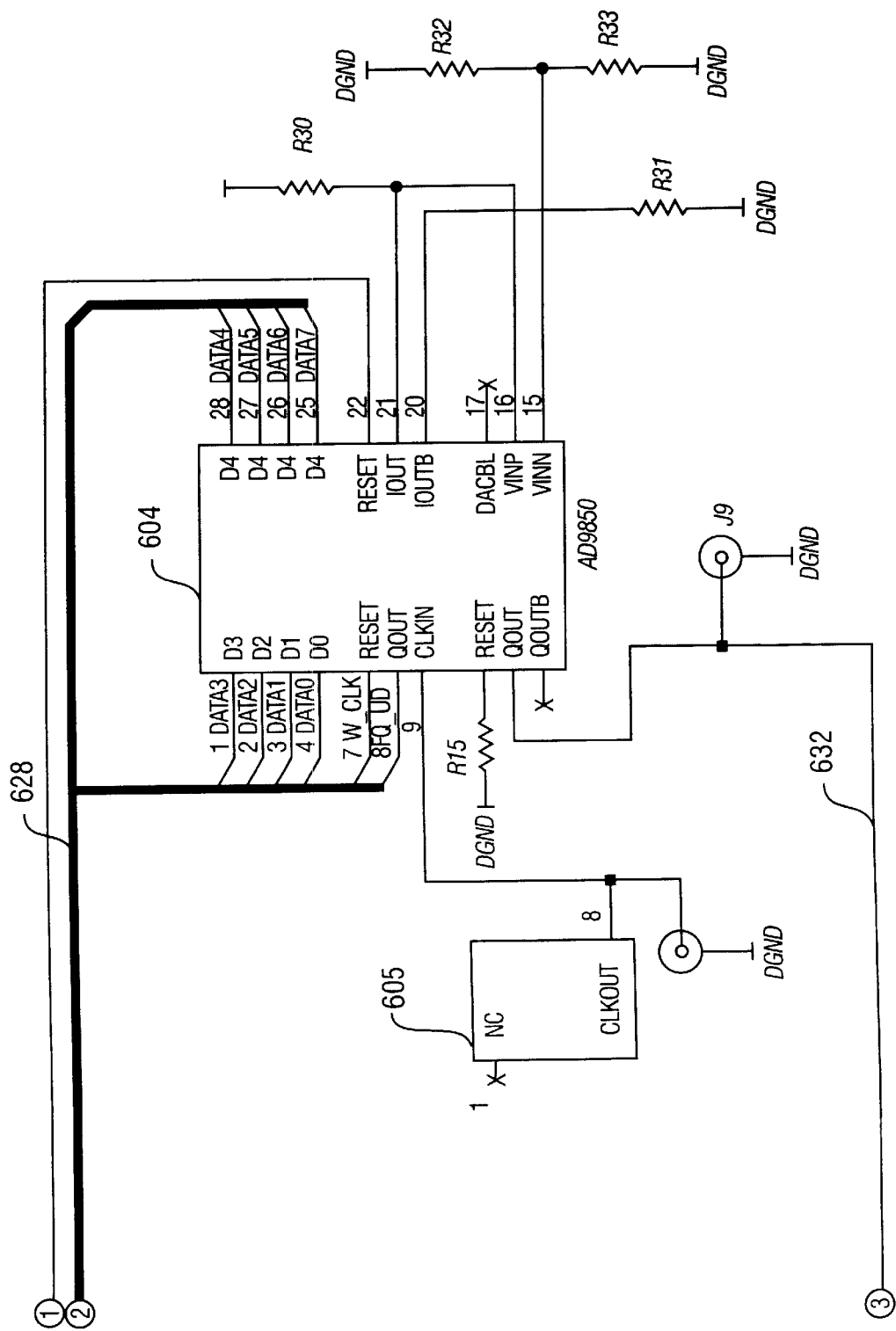
Figure 12C:
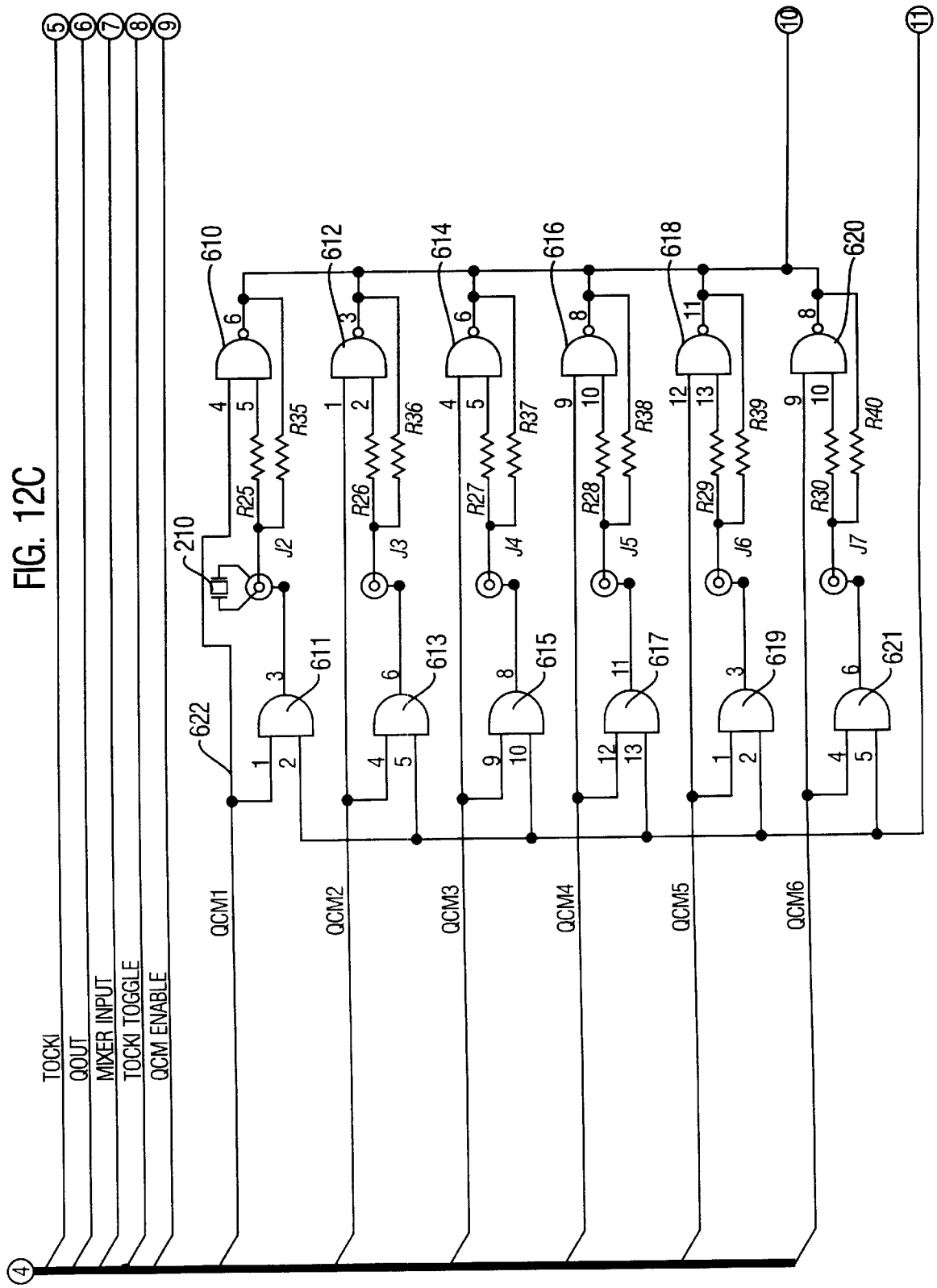
Figure 12D:
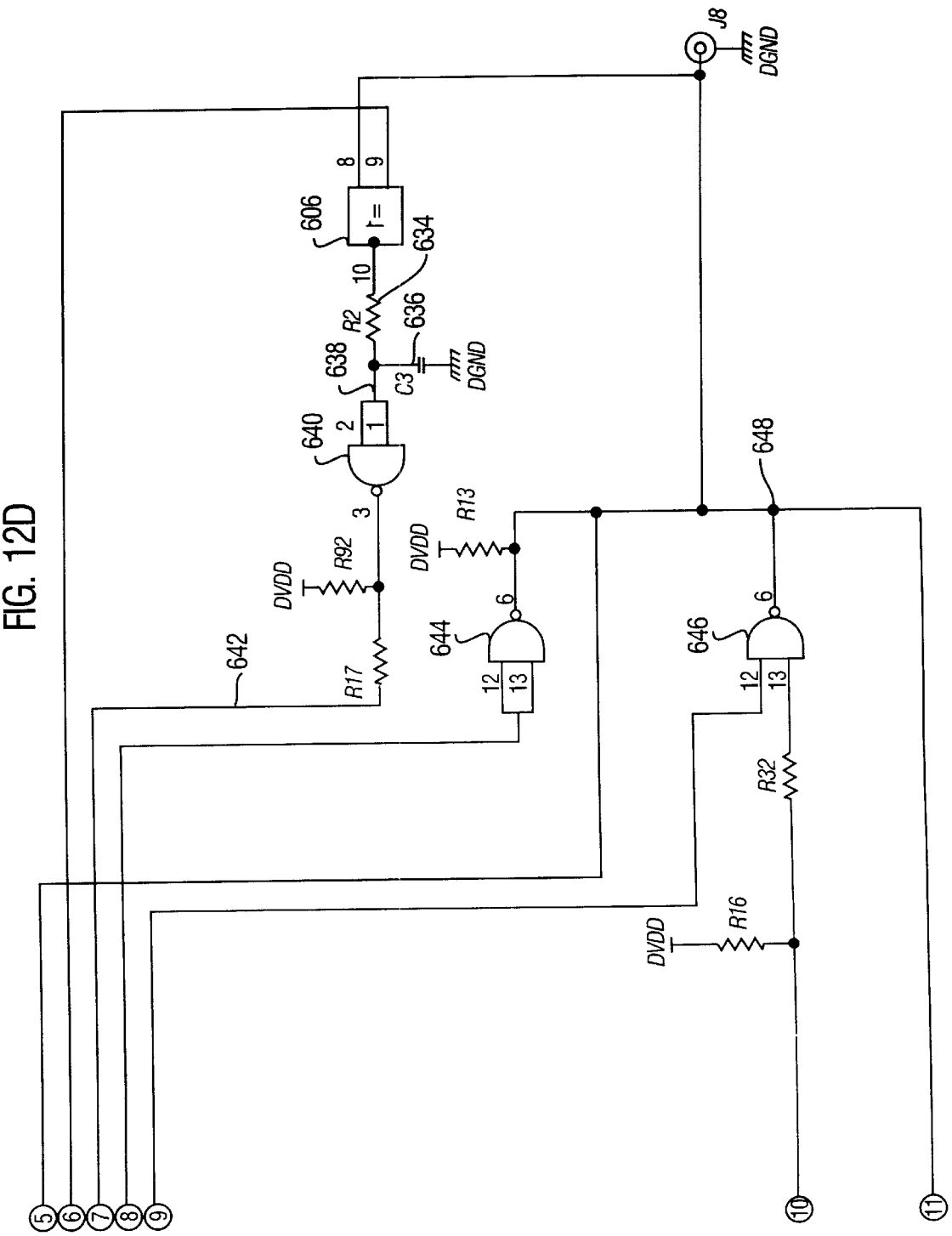

FIG. 11 is a diagram of typical waveforms of various signals generated by the high resolution frequency measurement circuit of FIG. 10. Waveform 560 represents the QCM frequency 502. This is a square wave oscillating at the resonant frequency of the QCM gas sensor 210. The frequency of waveform 560 is a function of the mass of QCM gas sensor 210, which is a function of gas concentration.

Waveform 562 represents reference signal 522. This signal is generated by digital frequency synthesizer 520, and has a frequency determined by the value of coarse measurement 518. Waveform 562 has a lower frequency than waveform 560, because coarse measurement 518 is always less than QCM frequency 502.

Waveform 564 represents the output from digital mixer 506. This waveform is a pulse-width modulated signal created by the phase variance between waveform 560 (QCM frequency 502) and waveform 562 (reference signal 522). The pulse width of waveform 564 varies sinusoidally, and the period of the sinusoidal variation is a function of the difference in frequency between waveform 560 and waveform 562.

Waveform 566 represents the output from low-pass filter 528. The pulses of waveform 566 are integrated by the low-pass filter 526, removing the high frequency carrier and converting the sinusoidal variation of pulse width of waveform 564 into low frequency sinusoidal waveform 566. The frequency of waveform 566 equals the difference in frequency between waveform 560 and waveform 562.

Waveform 568 represents the difference frequency signal 532. Waveform 568 is generated by passing the sinusoidal waveform 566 through logic gate 530 to produce a square wave having the same frequency as waveform 566. Thus, waveform 568 is a square wave having a frequency equal to the difference in frequency between waveform 560 (QCM frequency 502) and waveform 562 (reference signal 522).

Turning now to FIGS. 12A–12D, a circuit to implement a high resolution frequency measurement circuit is shown. The circuit has three main components: a PIC embedded controller 602, a direct digital synthesis (DDS) integrated circuit 604, and a digital mixer 606. The embedded controller 602 contains two 8-bit counter-timers and a 16-bit counter-timer. The embedded controller 602 also contains program and variable memory to provide for control of the counter-timers and analysis of their outputs, and includes a communications port, either serial or parallel, and external address and data bus. The embedded controller 602 also should be capable of executing floating point math algorithms. A suitable controller is the PIC16C62 controller made by Microchip Technology Inc. of Arizona, although other controllers having the required functionality may also be used.

The DDS circuit 604 must be capable of creating periodic waveforms (square or sinusoidal) at frequencies equal to the resonating frequency of a QCM gas sensor. A monolithic DDS integrated circuit model AD9850, made by Analog Devices, Inc. of Massachusetts, is suitable for this application. The AD9850 generates the desired signal with 32-bit resolution. The digital mixer 606 is a single Boolean Exclusive OR gate, of a commonly available type.

Embedded controller 602 is connected to address decoder 608 which is connected to the sensor select gates 610, 612, 614, 616, 618, and 620, and to sensor isolation gates 611, 613, 615, 617, 619, and 621. The sensor select gates and sensor isolation gates each connect to a terminal of a QCM gas sensor and operate to connect the sensors into or isolate the sensors from the high resolution frequency measurement circuit. The following describes the detailed connections and operation of only one of the QCM gas sensors and its sensor select gate and sensor isolation gate, although it can be readily appreciated that additional sensors may be connected similarly and operated in the same manner, and that the high resolution frequency measurement circuit is designed to operate with multiple sensors.

QCM gas sensor 210 has a first terminal 218 (shown in FIG. 6) connected to a first input of sensor select gate 610, and a second terminal 220 (shown in FIG. 6) connected to the output of sensor isolation gate 611. The second input to the sensor select gate 610 and one input from sensor isolation gate 611 are both connected to sensor select line 622 from address decoder 608. Address decoder 608 is connected to controller 602 via sensor select lines 624 and 626. To select a particular sensor to measure, controller 602 generates a select signal on line 624 and a sensor address on lines 626 which is decoded by address decoder 608. Address decoder 608 outputs a high signal on the sensor select line corresponding to the selected sensor (and a low signal on all the other sensor enable lines), causing the corresponding sensor select gate and sensor isolation gate to connect the selected sensor to the oscillator circuit. Thus, to select QCM gas sensor 210, a select signal is generated by embedded controller 602 which causes address decoder 608 to output a high signal on sensor enable line 622. This high signal causes sensor select gate 610 and sensor isolation gate 611 to pass logic signals from QCM sensor 610 to oscillator NAND gate 646, completing the oscillator circuit through the QCM gas sensor 610 and providing feedback from the QCM gas sensor 610 to permit sustained oscillation at the resonant frequency of the sensor. In this way, multiple QCM gas sensors may be connected in parallel across the oscillator circuit, with the sensors being selected one at a time for measurement by embedded controller 602. Alternatively, other common digital techniques may be employed to individually select the sensors.

Upon selection of one of the QCM gas sensors, embedded controller 602 generates a QCM enable signal to enable operation of oscillator NAND gate 646. The oscillator output 648 (this is equivalent to the oscillator output 244 shown in FIG. 6) is connected to a timer-counter input of embedded controller 602. Because the particular model of embedded controller used in this embodiment does not have a 16-bit timer-counter that can be used to generate a coarse measurement of oscillator output 648 (i.e. the function performed by counter 504 in the circuit of FIG. 10), two 8-bit timer-counters are used. The first 8-bit timer-counter (the "8-bit prescaler") counts every cycle of oscillator output 648. The second 8-bit timer-counter increments only after a preset number of cycles (the "8-bit counter"). In this application, the 8-bit counter increments only once every 256 cycles of the oscillator output 648. Together, the 8-bit counter and 8-bit prescaler provide a 16-bit count of oscillator output 648; the 8-bit prescaler providing the least significant 8 bits and the 8-bit counter providing the most significant 8 bits of the 16-bit count. The outputs from the 8-bit counter and 8-bit prescaler are concatenated by the embedded controller 602 to yield a 16 bit count. This count is the initial frequency measurement 514, described above in the discussion of FIG. 10.

The following example illustrates the method of deriving a full 16 bit count from outputs of the 8-bit counter and 8-bit prescaler. If the oscillator output 648 is 9 MHz and the gate time is 6 ms, then the number of counts recorded by the 8-bit counter is $(9 \times 10^6 \text{ Hz}) \times (6 \times 10^{-3} \text{ s})/256 = 210.9375$ counts. The 8-bit counter increments every 256 cycles of the oscillator output 648, yielding a counter value of 210 or D2 [base 16]. This value is the upper 8 bits of the total 16-bit count of initial frequency measurement 514. The 8-bit prescaler increments on every cycle of the oscillator output 648. The 8-bit prescaler rolls over at 256 counts, so the number of counts recorded is the fractional count (the count remaining in the counter at the end of the 6 ms gate period), equal to $0.9375 \times 256$, which equals 240 [base 10] or F0 [base 16]. This value is the lower 8 bits of the 16-bit initial frequency measurement 514. The full 16 bit value is thus D2F0 [base 16].

However, the embedded controller 602 can only access the count accumulated by the 8-bit counter. To derive the full 16-bit count, embedded controller 602 performs the following steps. First, embedded controller 602 sends a QCM enable signal (i.e. a high logic voltage) to oscillator NAND gate 646 for a 6 millisecond gate period. During this period, the 8-bit counter and 8-bit prescaler count the pulses appearing at oscillator output 648. At the end of the gate period, the QCM enable signal is removed which disables the oscillation of oscillator output 648, and embedded controller 602 stores the count accumulated by the 8-bit prescaler. To determine the count accumulated by the 8-bit prescaler, embedded controller 602 then toggles the input to NAND gate 644 from high to low, causing oscillator output 648 to toggle from low to high, which causes the 8-bit prescaler to accumulate additional counts. Embedded controller 602 continues to toggle the input to NAND gate 644 until the 8-bit prescaler overflows, causing the 8-bit counter count to increase by one count. Embedded controller 602 then subtracts the number of toggles required to cause this overflow from 256 to calculate the count accumulated by the 8-bit prescaler during the 6 millisecond gate period. Lastly, embedded controller concatenates this derived count with the stored count from the 8-bit counter to result in the 16 bit initial frequency measurement 514.

The frequency of the oscillator output 648 will be the frequency at which the QCM gas sensor is resonating, typically 9 MHz, and the model of embedded controller 602 used in this embodiment cannot measure such a high frequency directly. The internal clock of the embedded controller 602 is limited to one fourth the rate of the master clock frequency, resulting in an internal clock frequency of 5 MHz for a typical master clock frequency of 20 MHz. To permit the embedded controller 602 to measure the 9 MHz frequency, the oscillator output 648 is used as the clock input to the 8-bit counter and 8-bit prescaler, and a fixed frequency signal having a 6 ms period is generated from the internal clock and is used as the other input. In this configuration, the 8-bit counter and 8-bit prescaler count the number of cycles of oscillator output 648 occurring during a 6 ms gate period.

The 16 bit count of cycles occurring during the gate period is the initial measurement 514 of the frequency of oscillator output 648. Embedded controller 602 subtracts one count to from initial measurement 514 to produce coarse count. The embedded controller 602 then performs a floating point calculation to convert the integer coarse count to coarse measurement 518 in engineering units. The coarse count is divided by the gate period to convert the integer count value into a frequency value. For example, a QCM frequency of 9.12345 MHz and a 6 millisecond gate period will result in a initial measurement 514 of: 9.12345 MHz× $6\times 10^{-3}$ s=54740 [base 10] or D5D4 [base 16]. Subtracting one count yields a coarse count of D5D3 [base 16]. Thus, the coarse measurement 518 in engineering units is: D5D3 [base 16]×$6\times 10^{-3}$ s=9.123166667 MHz.

However, the DDS 604 requires an integer input scaled to its clock frequency. To produce the DDS input, the embedded controller 602 converts the engineering unit coarse measurement 518 into an integer control word for input to the DDS 604. The DDS control word is calculated by multiplying the coarse measurement 518 by the full-scale count value of the 32-bit DDS 604, and dividing by the DDS clock frequency. For example, using the data given above and assuming the DDS 604 has a clock frequency of 50 MHz, the DDS control word would be: 9.123166667 MHz× $2^{32}$/50 MHz=783,674,049 [base 10] or 2EB5EAC1 [base 16].

The embedded control transmits the DDS control word and control signals on data lines 628 to DDS 604. DDS 604 generates reference frequency 522 (shown in FIG. 2) having a frequency equal to the frequency represented by the control word (which is the same frequency as that represented by coarse measurement 518) from embedded controller 602, transmitting the result on DDS output 632. Digital mixer 606 receives DDS output 632 (the reference frequency 522) and oscillator output 648 (the QCM frequency 502). The digital mixer 606 performs an Exclusive OR operation on the two inputs to produce a pulse width modulated output. This output passes through a simple single-pole filter comprising resistor 634 and capacitor 636. The output 638 from the low pass filter 526 is fed to buffer 640, comprising an open collector NAND gate, to provide a square wave at output 642 to the 16 bit counter-timer of embedded controller 602.

The 16 bit counter-timer circuit produces a fine count. Embedded controller 602 converts the integer fine count into fine measurement 536 in engineering units by dividing the embedded controller 602 internal clock frequency by the fine count. For example, if the embedded controller clock frequency is 5 MHz, a fine count of 17647 [base 50] or 44EF [base 16] would yield a fine measurement 536 of: 5 MHz/ 44EF=283.334 Hz. Because the fine count (representing the difference frequency 524 of FIG. 10) is much less than internal clock frequency of the embedded controller 602, the resulting fine measurement 536 has a very high resolution.

To calculate final measurement 540, embedded controller 602 performs a floating point add of coarse measurement 518 and fine measurement 536. Lastly, embedded controller 602 converts the floating point final measurement 540 into a format suitable for transmission over a serial communication link to a central monitoring system.

A typical reading profile involves enabling each of the individual QCM gas sensors one at a time taking a measurement for each one. A final measurement 540 is calculated for each QCM gas sensor and transmitted to the central monitoring system with appropriate information identifying which sensor generated the data.

Figure 13A:
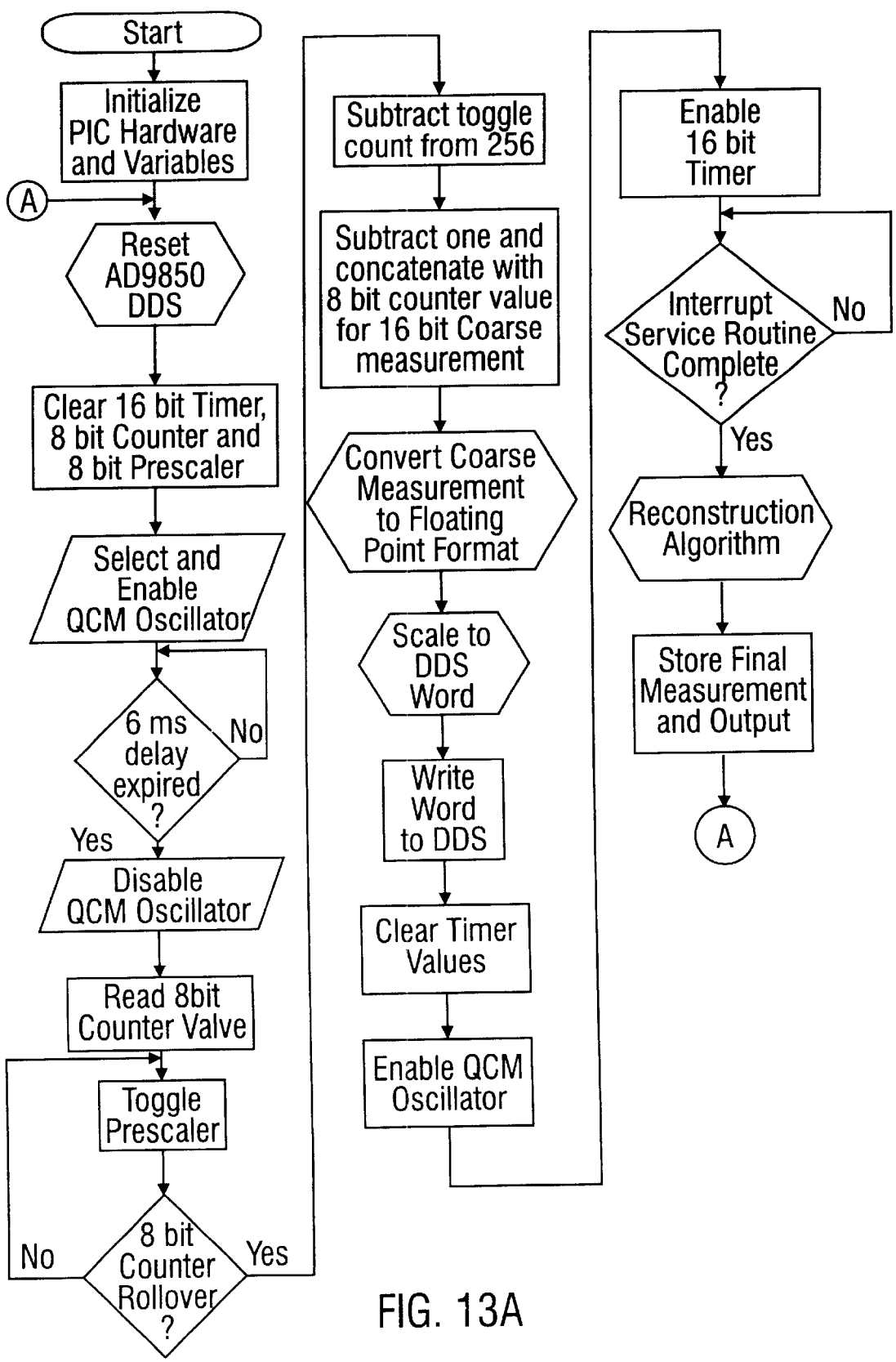
FIG. 13A is a flowchart of a software program used by the embedded controller of FIG. 12A to implement a high frequency measuring circuit.
Figure 13B:
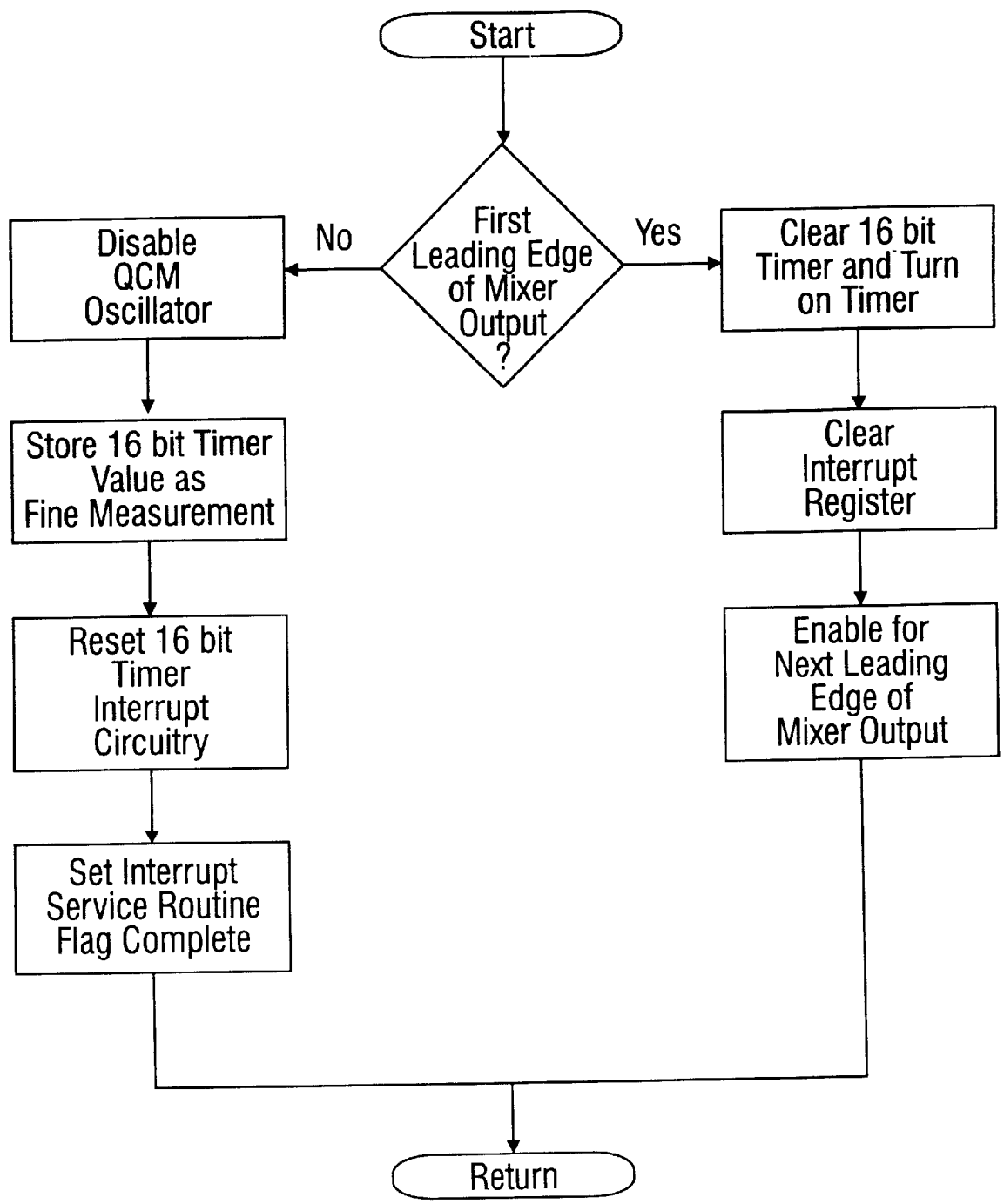
FIG. 13B is a flowchart of an interrupt service routine used by the embedded controller of FIG. 12A to implement a high frequency measuring circuit.

The above described functions of the embedded controller 602 may be implemented according to the software program flowchart depicted in FIG. 13A and the interrupt service routine flowchart depicted in FIG. 13B. FIG. 13A shows the main program which executes cyclically to implement the high frequency measuring circuit. Upon initial startup, the PIC embedded controller 602 is initialized and the variables stored within the PIC embedded controller 602 are reset. The program then enters a loop, beginning with a reset of the DDS 604 and clearing of the embedded controller's 16 bit timer, 8-bit counter, and 8-bit prescaler values. A QCM gas sensor is then selected for measurement and an enable signal sent to the oscillator NAND gate 646 to enable the QCM oscillator circuit.

At the end of a 6 millisecond delay, a disable signal is sent to the oscillator NAND gate 646, the accumulated count value of the 8-bit counter is read and temporarily stored by the embedded controller 602. The embedded controller 602 then sends signals to toggle the input to NAND gate 644 to cause the 8-bit prescaler to accumulate additional counts. The toggle signals are sent until the 8-bit counter increments by one count. The embedded controller 602 keeps an accumulated count of the number of toggle signals sent and subtracts this count from 256. One count is then subtracted from the resulting value, and it is concatenated with the previously stored 8-bit counter value to give a 16 bit coarse measurement. This coarse measurement is then converted to floating point format and scaled to produce a word suitable for input to the DDS 604. The 16 bit timer of the embedded controller 602 is cleared, an enable signal sent to the oscillator NAND gate 646, and the 16 bit timer enabled.

The program then waits for the interrupt service routine, shown in FIG. 13B and described below, to complete. The output from digital mixer 606 drives the input to the interrupt circuit, and completion of the interrupt service routine indicates that one complete cycle of the output of digital mixer 606 has occurred and the 16-bit timer has accumulated a fine measurement count. The embedded controller 602 then performs the reconstruction algorithm to derive the final measurement from the coarse measurement and fine measurement values previously obtained. The embedded controller 602 stores the final measurement value and outputs the value onto the embedded controller's data bus. The program execution then returns to the beginning of its loop, resets the DDS 604, and continues execution as described above.

The interrupt service routine shown in FIG. 13B starts when a leading (or rising) edge of the output from digital mixer 606 is detected by the embedded controller 602 and an interrupt signal generated. The first execution of the interrupt service routine will proceed down the right leg of the flowchart. The 16-bit timer is cleared and turned on, the interrupt register cleared and enabled to permit detection of a second leading edge of the output from digital mixer 606. The second execution of the interrupt service routine, triggered by detection of a second leading edge of the output of digital mixer 606, begins execution of the left leg of the flowchart. A disable signal is first sent to oscillator NAND gate 646 to disable the QCM oscillator circuit. The embedded controller 602 then stores the accumulated value from the 16-bit timer as the fine measurement. The 16-bit timer is reset, the interrupt circuitry is reset, and a flag is set to indicate that the interrupt service routine has completed.

The flowcharts illustrate one method of programming the embedded controller 602 to implement the high frequency measuring circuit of the present invention, although many other methods may be used that will be apparent to one of ordinary skill in the art.

4. Thermodynamic Sensor Interface

The thermodynamic sensor interface circuit 700 receives signals from the thermodynamic sensor array 280, which may comprise temperature sensor 282, relative humidity sensor 284, and differential pressure sensor 286. The thermodynamic sensor interface circuit 700 processes the sensor signals to generate digital signals representing the measured variables. The temperature sensor 282 and relative humidity sensor 284 are preferably QCM devices, and the interface circuits for these sensors operate similarly to the QCM gas sensor interface circuit shown in FIG. 10, 11, and 12D—12D and described above. The interface circuit for the differential pressure sensor 286 uses components and techniques known to one of skill in the art.

5. The Remote Calibrator Control Circuit

The remote calibrator control circuit 750 controls operation of the remote to calibration system 300. The remote calibrator control circuit 750 may receive commands from the microcontroller 404, or directly from the plant control system 40. When it receives a command to initiate a calibration cycle of the gas sensor array 200, the remote calibrator control circuit 750 activates the thermal activator 326, the actuator 331 of outlet valve 330, and actuator 333 of second valve 332 or remote calibration system 300 (shown in FIG. 8) in a timed sequence in order to inject calibrant in the sensor chamber 114.

6. Communication Interface Circuit

The communication interface circuit 800 provides a means to send data from the fugitive emission sensing system 10 to a remote plant process control system 40, and to receive data and control signals from the plant process control system 40. The data sent to the process control system 40 may include measurement data from the gas sensor array 200 and thermodynamic sensor array 280, and calibration data for the sensor arrays. The data and control signals received from the process control system 40 may include commands to take emission measurements, commands to perform a calibration of the sensors, and commands to download stored measurement and calibration data.

The fugitive emission sensing system 10 may also be integrated with the valve it is monitoring so that the communication interface circuit 800 may also send valve stem position data and other valve related data to the process control system 40, and may receive valve position control signals from the process control system 40. This data exchange between the fugitive emission sensing system 10 and the plant control system 40 may include any operational or maintenance data appropriate to the equipment integrated with fugitive emission sensing system 10.

The preferred method of communicating data between the fugitive emission sensing system 10 and the plant process control system 40 is by means of a single two-conductor communication link, although other communication links, including fiber optic cabling, may be used. The communication interface circuit 800 may use the communication link to send and receive both analog and digital signals. For example, an analog 4–20 milliamp signal may be used to send a valve position output from the plant control system 40 to a control valve integrated with the fugitive emission sensing system 10, where the 4–20 milliamp signal is used to modulate a compressed air supply to control the valve stem position. The same two-wire cable may also used to exchange data in digital format between the fugitive emission sensing system 10 and the process control system 40. A suitable communication interface circuit for use with the fugitive emission sensing system 10 is described in U.S. Pat. No. 5,451,923, the disclosure of which is hereby incorporated by reference in its entirety. Another communication interface circuit is described in U.S. Pat. No. 5,434,774, the disclosure of which is hereby incorporated by reference in its entirety.

The fugitive emission sensing system 10 may use gas sensor measurement data to take control actions designed to reduce or eliminate emissions from the plant. This may include shutting off the stream of fluid passing through an emissions source from which emissions have been detected, or changing the operational state of the emissions source itself to reduce the possibility of continuing emissions. The plant process control system 40 also may use gas sensor measurement data received from the fugitive emissions sensing system 10 to take control actions designed to reduce or eliminate emissions from the plant.

7. Power Conversion Circuit

The power conversion circuit 900 provides power to the fugitive emission sensing system 10. The power conversion circuit 900 performs voltage conversion and regulation of incoming power to provide a regulated and continuous power to the fugitive emission sensing system 10. The power conversion circuit 900 may receive power from an auxiliary power supply line or a battery integrated into the fugitive emission sensing system 10, or may use the signal generated by the plant control system 40 to provide power. A suitable circuit for utilizing the voltage on the communication link to the plant control system 40 is described in U.S. Pat. No. 5,451,923, the disclosure of which is hereby incorporated by reference. Other techniques and circuits that may be used for the power conversion circuit 900 are well known to those of skill in the art.

Many modifications and variations may be made in the techniques and structures described and illustrated herein without departing from the spirit and scope of the present invention. Accordingly, it should be understood that the methods and apparatus described herein are illustrative only and are not limiting upon the scope of the present invention.

What is claimed is:

1. A system for collecting data relating to emissions from an emissions source comprising:
    an accumulator adapted to receive emissions from said emissions source, said accumulator having an outlet;
    a sensor chamber connected to said outlet of said accumulator to receive said emissions therefrom, said sensor chamber having an outlet;
    an ejector connected to said outlet of said sensor chamber, said ejector adapted to draw said emissions from said accumulator, through said sensor chamber, and into said ejector;
    at least one sensor disposed within said sensor chamber and in flow communication with said outlet of said accumulator for generating a signal indicative of a physical property of said emissions; and
    a sensor interface circuit adapted to receive said signal for generating data relating to said emissions from said emissions source.

2. The system of claim 1 wherein said physical property of said emissions generated by said at least one sensor is the concentration of said emissions.

3. The system of claim 1 further comprising an ejector in flow communication with said outlet of said accumulator, said ejector adapted to draw said emissions from said accumulator to expose said at least one sensor to said emissions.

4. The system of claim 3 wherein said ejector is connectable to a source of pressurized fluid whereby said pressurized fluid flows through said ejector thereby creating a pressure drop to draw said emissions from said accumulator into said ejector.

5. The system of claim 4 wherein said ejector comprises a primary nozzle and a secondary nozzle, said primary nozzle adapted to receive said pressurized fluid and discharge said pressurized fluid into said secondary nozzle.

6. The system of claim 5 further comprising a microregulator to regulate the pressure of said pressurized fluid before said primary nozzle receives said pressurized fluid.

7. The system of claim 1 further comprising a source of calibrant in flow communication with said sensor chamber.

8. The system of claim 1 wherein said emissions source comprises a valve having valve stem packing, said valve stem packing having an exterior surface, wherein said accumulator circumferentially encloses said exterior surface of said valve stem packing of said valve.

9. The system of claim 1 wherein said data generated by said sensor interface circuit is derived by measuring the frequency of said signal generated by said at least one sensor.

10. The system of claim 9 wherein said sensor interface circuit comprises:
 a counter connectable to said signal generated by said sensor for generating a coarse measurement of said frequency of said signal;
 a frequency synthesizer connected to said counter for generating a reference signal having a frequency equal to the frequency represented by said coarse measurement;
 a difference circuit connected to said frequency synthesizer for generating a fine measurement representing the difference in frequency between said input signal and said reference signal; and
 a summing circuit connected to said counter and said difference circuit, for summing said coarse measurement and said fine measurement, thereby obtaining a final measurement indicative of said frequency of said input signal.

11. The system of claim 10 wherein said frequency of said reference signal is lower than said frequency of said signal generated by said sensor.

12. The system of claim 11 wherein said counter generates an initial measurement approximating said frequency of said signal generated by said sensor and changes said initial measurement by a predetermined amount to obtain said coarse measurement.

13. The system of claim 12 wherein said input signal is generated by a gas sensor and said final measurement is indicative of the concentration of a gas.

14. The system of claim 1 wherein at least one of said at least one sensors comprises a quartz crystal microbalance gas sensor.

15. The system of claim 1 wherein at least one of said at least one sensors comprises a thermodynamic sensor.

16. The system of claim 15 wherein said thermodynamic sensor comprises a sensor selected from the group consisting of a temperature sensor, a relative humidity sensor, and a differential pressure sensor.

17. The system of claim 1 further comprising a sensor calibrator in flow communication with said at least one sensor for storing a calibrant and exposing said at least one sensor to said calibrant.

18. The system of claim 17 wherein said sensor calibrator comprises:
 a reservoir for storing a calibrant;
 a conduit in flow communication with said reservoir, a portion of said conduit defining a dosing chamber for storing a measured quantity of said calibrant;
 an outlet nozzle in flow communication with said dosing chamber; and
 a thermal activator adjacent said dosing chamber for vaporizing said measured quantity of calibrant in said dosing chamber and ejecting said measured quantity through said outlet nozzle.

19. The system of claim 18 further comprising a remotely operated valve at said outlet nozzle for isolating said dosing chamber from the surrounding atmosphere.

20. The system of claim 19 further comprising a remotely operated valve disposed between said reservoir and said dosing chamber for isolating said reservoir from said dosing chamber.

21. The system of claim 20 wherein said valves are electrically operated, and further comprising a control circuit for remotely operating said valves and for energizing said thermal activator.

22. The system of claim 17 further comprising:
 a microcontroller adapted to receive said data from said sensor interface circuit; and
 a memory connected to said microcontroller for storing data from said sensor interface circuit where said data is derived from said at least one sensor's response to said calibrant.

23. The system of claim 1 further comprising a microcontroller adapted to receive said data from said sensor interface circuit.

24. The system of claim 23 further comprising a memory connected to said microcontroller for storing said data from said sensor interface circuit.

25. The system of claim 24 further comprising a communication interface circuit connected to said microcontroller for sending said data to a process control system.

26. The system of claim 25 wherein said communication interface circuit receives signals from a process control system for control of said system for collecting data.

27. The system of claim 25 further comprising a power conversion circuit connected to said sensor interface circuit, microcontroller, and communication interface circuit, said power conversion circuit providing a voltage to said sensor interface circuit, microcontroller, and communication interface circuit generated from said signals received from said process control system.

28. The system of claim 1, wherein the accumulator comprises a collecting tube adapted to be situated adjacent said emissions source, said collecting tube having a closed first end and a second end defining said outlet, said collecting tube defining at least one orifice for receiving said emissions.

29. The system of claim 28, wherein said at least one orifice comprises a plurality of orifices.

30. The system of claim 1, wherein the accumulator comprises a capsule adapted to enclose at least a portion of said emissions source.

31. The system of claim 30, wherein the capsule further comprises a baffle situated adjacent said outlet, the baffle adapted to prevent foreign particles entering the outlet.

32. A method for collecting data relating to emissions from an emissions source comprising:
 creating a pressure drop to draw said emissions from said emissions source into an accumulator, through a sensor chamber, and into an ejector to collect at least a portion of said emissions;
 exposing at least one sensor disposed within said sensor chamber to said collected emissions to generate a signal indicative of a physical property of said emissions; and
 processing said signal generated by said at least one sensor to generate data relating to said emissions from said emissions source.

33. The method of claim 32 wherein said physical property of said emissions generated by said at least one sensor is the concentration of said emissions.

34. The method of claim 32, wherein creating said pressure drop comprises:

providing an ejector in flow communication with said accumulator; and supplying pressurized fluid to said ejector, thereby creating a pressure drop in said ejector and drawing said emissions from said emissions source into said accumulator, thereby exposing said at least one sensor to said emissions.

35. The method of claim 32 further comprising sending said data relating to said emissions to a process control system.

36. A system for collecting data relating to emissions from an emissions source comprising:

an accumulator adapted to receive emissions from said emissions source, said accumulator having an outlet;

at least one sensor in flow communication with said outlet of said accumulator for generating a signal indicative of a physical property of said emissions; and a sensor interface circuit adapted to receive and measure the frequency of said signal for generating data relating to said emissions from said emissions source, said sensor interface circuit comprising:

a counter connectable to said signal generated by said sensor for generating a coarse measurement of said frequency of said signal;

a frequency synthesizer connected to said counter for generating a reference signal having a frequency equal to the frequency represented by said coarse measurement;

a difference circuit connected to said frequency synthesizer for generating a fine measurement representing the difference in frequency between said input signal and said reference signal; and a summing circuit connected to said counter and said difference circuit, for summing said coarse measurement and said fine measurement, thereby obtaining a final measurement indicative of said frequency of said input signal.

37. The system of claim 36 wherein said frequency of said reference signal is lower than said frequency of said signal generated by said sensor.

38. The system of claim 37 wherein said counter generates an initial measurement approximating said frequency of said signal generated by said sensor and changes said initial measurement by a predetermined amount to obtain said coarse measurement.

39. The system of claim 38 wherein said input signal is generated by a gas sensor and said final measurement is indicative of the concentration of a gas.

40. A system for collecting data relating to emissions from an emissions source comprising:

an accumulator adapted to receive emissions from said emissions source, said accumulator having an outlet;

at least one sensor in flow communication with said outlet of said accumulator for generating a signal indicative of a physical property of said emissions;

a sensor interface circuit adapted to receive said signal for generating data relating to said emissions from said emissions source; and a sensor calibrator in flow communication with said at least one sensor for storing a calibrant and exposing said at least one sensor to said calibrant; said sensor calibrator comprising:

a reservoir for storing a calibrant;

a conduit in flow communication with said reservoir, a portion of said conduit defining a dosing chamber for storing a measured quantity of said calibrant;

an outlet nozzle in flow communication with said dosing chamber; and a thermal activator adjacent said dosing chamber for vaporizing said measured quantity of calibrant in said dosing chamber and ejecting said measured quantity through said outlet nozzle.

41. The system of claim 40 further comprising a remotely operated valve at said outlet nozzle for isolating said dosing chamber from the surrounding atmosphere.

42. The system of claim 41 further comprising a remotely operated valve disposed between said reservoir and said dosing chamber for isolating said reservoir from said dosing chamber.

43. The system of claim 42 wherein said valves are electrically operated, and further comprising a control circuit for remotely operating said valves and for energizing said thermal activator.

44. A system for collecting data relating to emissions from an emissions source comprising:

a collecting tube shaped to circumferentially enclose said emissions source and receive emissions therefrom, said collecting tube having a closed first end and a second end defining an outlet, said collecting tube defining a plurality of orifices for receiving said emissions; said orifices defining respective diameters that increase as the position of the respective orifice increases from said first end;

at least one sensor in flow communication with said outlet for generating a signal indicative of a physical property of said emissions; and a sensor interface circuit adapted to receive said signal for generating data relating to said emissions from said emissions source.

45. The system of claim 44 further comprising an ejector in flow communication with said outlet, said ejector adapted to draw said emissions from said collecting tube to expose said at least one sensor to said emissions.

46. The system of claim 45 further comprising a sensor chamber disposed between said outlet and said ejector, said at least one sensor disposed within said sensor chamber, said emissions being drawn from said collecting tube, through said sensor chamber, and into said ejector.

47. A system for collecting data relating to emissions from an emissions source comprising:

an accumulator adapted to receive emissions from said emissions source, said accumulator having an outlet;

at least one sensor in flow communication with said outlet of said accumulator for generating a signal indicative of a physical property of said emissions;

an ejector in flow communication with said outlet of said accumulator, said ejector having a primary nozzle connectable to receive pressurized fluid and discharge said pressurized fluid into a secondary nozzle thereby creating a pressure drop to draw said emissions from said accumulator into said ejector to expose said at least one sensor to said emissions;

a microregulator coupled to regulate the pressure of said pressurized fluid before said primary nozzle receives said pressurized fluid; and a sensor interface circuit adapted to receive said signal for generating data relating to said emissions from said emissions source.

* * * * *